(12) United States Patent
Hu et al.

(10) Patent No.: US 9,238,643 B2
(45) Date of Patent: Jan. 19, 2016

(54) AMIDE COMPOUNDS

(75) Inventors: Wenhui Hu, Guangzhou (CN); Guifa Zhong, Guangzhou (CN); Ling Yang, Nanjing (CN); Hongjiang Xu, Nanjing (CN)

(73) Assignee: Guangzhou Institutes of Biomedicine and Health, Chinese Academy of Sciences, Guangdong (CN)

( * ) Notice: Subject to any disclaimer, the term of this patent is extended or adjusted under 35 U.S.C. 154(b) by 4 days.

(21) Appl. No.: 13/821,165

(22) PCT Filed: Sep. 6, 2010

(86) PCT No.: PCT/CN2010/076652
§ 371 (c)(1),
(2), (4) Date: May 13, 2013

(87) PCT Pub. No.: WO2012/031383
PCT Pub. Date: Mar. 15, 2012

(65) Prior Publication Data
US 2013/0245033 A1    Sep. 19, 2013

(51) Int. Cl.
| | |
|---|---|
| A61K 31/501 | (2006.01) |
| C07D 403/06 | (2006.01) |
| C07D 237/24 | (2006.01) |
| C07D 409/06 | (2006.01) |
| C07D 403/12 | (2006.01) |
| C07D 207/34 | (2006.01) |
| C07D 231/14 | (2006.01) |
| C07D 231/56 | (2006.01) |
| C07D 239/74 | (2006.01) |
| C07D 333/38 | (2006.01) |
| C07D 401/12 | (2006.01) |
| A61K 31/517 | (2006.01) |
| A61K 31/496 | (2006.01) |
| C07D 401/06 | (2006.01) |

(52) U.S. Cl.
CPC ............ *C07D 403/12* (2013.01); *C07D 207/34* (2013.01); *C07D 231/14* (2013.01); *C07D 231/56* (2013.01); *C07D 237/24* (2013.01); *C07D 239/74* (2013.01); *C07D 333/38* (2013.01); *C07D 401/12* (2013.01); *C07D 403/06* (2013.01); *C07D 409/06* (2013.01)

(58) Field of Classification Search
None
See application file for complete search history.

(56) References Cited

U.S. PATENT DOCUMENTS

| 3,867,388 | A | 2/1975 | Schnettler et al. |
| 7,528,155 | B2 | 5/2009 | Zoller et al. |
| 7,718,663 | B2 | 5/2010 | Okano et al. |
| 7,772,268 | B2 | 8/2010 | Zoller et al. |
| 2007/0004750 | A1 | 1/2007 | Lorsbach et al. |
| 2008/0318959 | A1* | 12/2008 | Rekosh et al. ............ 514/247 |
| 2009/0325973 | A1 | 12/2009 | Watterson et al. |

FOREIGN PATENT DOCUMENTS

| CN | 1944404 A | 4/2007 |
| CN | 1944424 A | 5/2010 |
| CN | 101754762 A | 6/2010 |
| CN | 101851211 A | 10/2010 |
| EP | 0 228 845 A2 | 7/1987 |
| EP | 1 300 399 A1 | 4/2003 |
| JP | 8-512284 A | 12/1996 |
| JP | 2001-510831 A | 8/2001 |
| JP | 2004-517145 A | 6/2004 |
| JP | 2004-203871 A | 7/2004 |
| JP | 2004-520434 A | 7/2004 |
| JP | 2005-500266 A | 1/2005 |
| JP | 2005-509627 A | 4/2005 |
| JP | 2006-508935 A | 3/2006 |
| JP | 2006-516656 A | 7/2006 |
| JP | 2007-503388 A | 2/2007 |
| JP | 2007-531755 A | 11/2007 |
| JP | 2007-532665 A | 11/2007 |
| JP | 2007-535488 A | 12/2007 |
| JP | 2007-537300 A | 12/2007 |
| JP | 2008-540575 A | 11/2008 |
| JP | 2009-504734 A | 2/2009 |
| JP | 2009-523769 A | 6/2009 |
| JP | 2010-513458 A | 4/2010 |
| JP | 2010-514693 A | 5/2010 |

(Continued)

OTHER PUBLICATIONS

CA Registry No. 1183695-63-7, entered into CA Registry File on Sep. 13, 2009, supplied by UkrOrgSynthesis.*
CA Registry No. 1183483-87-5, entered into CA Registry File on Sep. 13, 2009, supplied by UkrOrgSynthesis.*
CA Registry No. 1184254-35-9, entered into CA Registry File on Sep. 14, 2009, supplied by UkrOrgSynthesis.*
CA Registry No. 1184039-07-3, entered into CA Registry File on Sep. 14, 2009, supplied by UkrOrgSynthesis.*

(Continued)

*Primary Examiner* — Emily Bernhardt
(74) *Attorney, Agent, or Firm* — Seed IP Law Group PLLC

(57) ABSTRACT

A compound represented by formula (I) and the pharmaceutical acceptable salt thereof are disclosed,

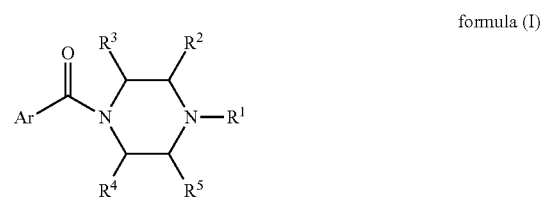

formula (I)

wherein, $R^1$, $R^2$, $R^3$, $R^4$, $R^5$ and Ar are defined as those in the specification.

8 Claims, No Drawings

(56) References Cited

FOREIGN PATENT DOCUMENTS

| | | | |
|---|---|---|---|
| JP | 2010-518042 A | | 5/2010 |
| JP | 2013-516428 A | | 5/2013 |
| JP | 2013-525376 A | | 6/2013 |
| WO | 01/53258 A1 | | 7/2001 |
| WO | 03/018563 A1 | | 3/2003 |
| WO | 03/091224 A1 | | 11/2003 |
| WO | 2004/035556 A1 | | 4/2004 |
| WO | 2004/055003 A1 | | 7/2004 |
| WO | 2004/080999 A1 | | 9/2004 |
| WO | 2005/073199 A1 | | 8/2005 |
| WO | 2005/076861 A2 | | 8/2005 |
| WO | 2005/079800 A1 | | 9/2005 |
| WO | 2005/105760 A1 | | 11/2005 |
| WO | 2006/003277 A1 | | 1/2006 |
| WO | 2006/032852 A1 | | 3/2006 |
| WO | 2006/081554 A2 | | 8/2006 |
| WO | 2006/124874 | * | 11/2006 |
| WO | 2006/124897 A2 | | 11/2006 |
| WO | 2007/042178 A1 | | 4/2007 |
| WO | 2007/050732 A1 | | 5/2007 |
| WO | 2007/082956 A1 | | 7/2007 |
| WO | 2007/137196 A2 | | 11/2007 |
| WO | 2008/067121 A2 | | 6/2008 |
| WO | 2008/096746 A1 | | 8/2008 |
| WO | 2009/025751 A1 | | 2/2009 |
| WO | 2009/055308 A1 | | 4/2009 |
| WO | 2010/010187 A1 | | 1/2010 |
| WO | 2010/084402 A2 | | 7/2010 |
| WO | 2010/084425 A1 | | 7/2010 |
| WO | 2011/018401 A1 | | 2/2011 |

OTHER PUBLICATIONS

UkrOrgSynthesis, Ltd. Product Guide, 1 page, retrieved from the Internet at https://www.molport.com/shop/supplier/UkrOrgSynthesis-Ltd/2076 on Sep. 6, 2014.*

CA Registry No. 848763-23-5, entered into CA Registry File on Apr. 19, 2005, supplied by Ambinter.*

CA Registry No. 848731-03-3, entered into CA Registry File on Apr. 19, 2005, supplied by Ambinter.*

CA Registry No. 848682-28-0, entered into CA Registry File on Apr. 18, 2005, supplied by Ambinter.*

Ambinter Product Guide,1 page, retrieved from the Internet at http://www.worldofchemicals.com/company/ambinter/15735.html on Dec. 22, 2014.*

Gahman et al. Chemical Abstracts, vol. 146 No. 13164 (Abstract for WO 2006/124874,Nov. 23, 2006) 2006.*

Hu et al., "Development of a novel therapeutic suppressor of brain proinflammatory cytokine up-regulation that attenuates synaptic dysfunction and behavioral deficits," Bioorganic & Medicinal Chemistry Letters 17: 414-418, 2007.

Rastogi et al., "Synthesis of 2-Substituted Quinazolines & Quinazolones as Potential Anthelmintics," Indian J. Chem 21B: 744-746, Aug. 1982.

CAPLUS abstract for JP 2006-056884, published Mar. 2, 2006, Accession No. 2006:192756, 3 pages.

Křupková et al., "Synthesis of Quinazolines from N-(2-nitrophenylsulfonyl)iminodiacetate and α-(2-Nitrophenylsulfonyl)amino Ketones via 2H-Inadazole 1-Oxides," J. Org. Chem. 75(13):4562-4566, 2010.

* cited by examiner

AMIDE COMPOUNDS

FIELD OF THE INVENTION

The present application relates to the field of organic chemistry and pharmaceutical chemistry, and more specifically to amide compounds.

BACKGROUND OF THE INVENTION

Nerve inflammatory disease mainly refers to the course triggered by neurospongium abnormality (microglial cell and astrocyte cell) or chronical activation. This kind of neurospongium with over-activating status causes high level falmmory and oxidative stress response molecules, resulting in injury or death of nerve cells. Injury or death of nerve cells may also induce activation of neurospongium, and boost locally harmful cycle propagation of nerve inflammation. Prior art has proven that nerve inflammatory response can be effectively restrained by suppression of neurospongium, especially microglia. Nerve inflammatory disease includes Senile Dementia (Alzheimer's disease), Parkinson's disease, Amyotrophic lateral sclerosis, autoimmune disease, Prion disease apoplexy, traumatic brain injury, spinal muscular atrophy, disseminated sclerosis, epilepsia, neuropathic pain, etc.

Senile Dementia is also named Alzheimer's disease (AD), the morbidity of which is No. 1 among all kinds of neurodegenerative diseases; AD is a central nervous system degenerative disease mainly causes progressive cognitive impairment and memory ability damage. The clinical manifestation of the disease is dysfunction of recent memory, following by persistent intelligence impairment, judgment and reasoning ability lose, aphasia, and dyskinesia etc. The pathological characteristics are a lot of senile plaques (SPs) and neurofibrilary tangles (NFTs).

Piperazine compounds have the function of selective inhibition of glial activation pathway (referring to WO03/018563). Chinese patent CN101754762 discloses piperazine compounds for treating nerve inflammatory diseases. Wenhui Hu et al. discloses minozac and a compound represented by formula (II) (referring to Bioorganic & Medicinal Chemistry Letters 17 (2007)414-418) having the activity against Senile Dementia.

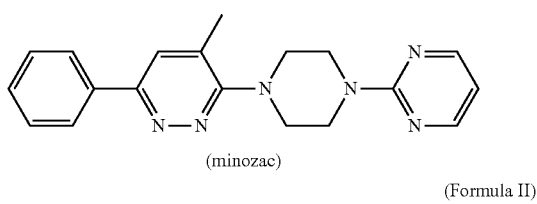

(minozac)

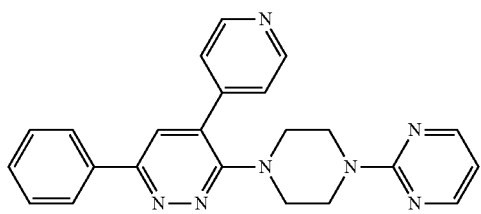

(Formula II)

SUMMARY

On one hand, the present application relates to a compound represented by formula (I) and the pharmaceutical salt thereof:

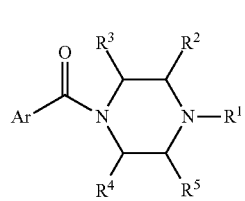

Formula (I)

Wherein, $R^1$ is hydrogen, substituted or unsubstituted alkyl, substituted or unsubstituted cycloalkyl, substituted or unsubstituted aryl, substituted or unsubstituted heterocyclic aryl, or substituted or unsubstituted heterocyclic alkyl;

$R^2$, $R^3$, $R^4$, $R^5$ are selected from a group of hydrogen, hydroxyl, azyl, nitryl, cyano group, halogen, alkyl, alkoxy, cycloalkyl, aryl, aryl alkyl, heterocyclic aryl or heterocyclic alkyl respectively; and Ar is a substituted or unsubstituted heterocyclic aryl, excluding benzpyrrole.

One the other hand, the present application relates to a compound represented by formula (I) and the pharmaceutical salt thereof:

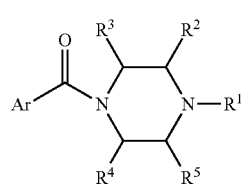

Formula (I)

Wherein, $R^1$ is a hydrogen, substituted or unsubstituted alkyl, substituted or unsubstituted cyclic alkyl, substituted or unsubstituted aryl, substituted or unsubstituted heterocyclic aryl, or substituted or unsubstituted heterocyclic alkyl, and the substituents thereof are selected from the group of aryl, aryl alkyl, alkyl, alkoxy, substituted alkyl, halogen, hydroxyl, azyl and cyanogroup;

$R^2$, $R^3$, $R^4$, $R^5$ are selected from the group of hydrogen, hydroxyl, azyl, nitryl, cyano group, halogen, alkyl, alkoxy, cycloalkyl, aryl, aryl alkyl, heteroaryl and heterocyclic alkyl, respectively; and Ar is a substituted or unsubstituted heterocyclic aryl, excluding benzpyrrole, and the substituents thereof are selected from the group of alkyl, alkoxy, halogenated alkyl, halogen, hydroxyl, azyl, aryl, aryl alkyl and aryloxy.

Furthermore, the present application relates to a method for preparing a compound represented by formula (I) and pharmaceutical salts thereof, comprising the reaction as following:

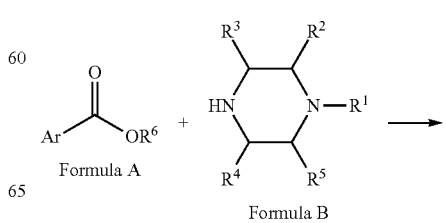

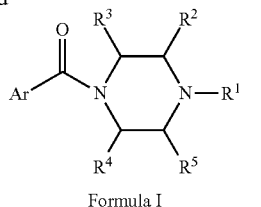

Formula I wherein $R^1$, $R^2$, $R^3$, $R^4$, $R^5$, Ar are defined the same as the above, $R^6$ is a hydrogen or alkyl. Also, the present application relates to a pharmaceutical composition, comprising treatment effective dose of a compound represented by formula (I) or the pharmaceutical acceptable salt and the pharmaceutical acceptable carrier thereof:

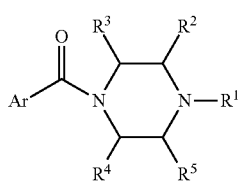

Formula (I)

Wherein, $R^1$ is a hydrogen, substituted or unsubstituted alkyl, substituted or unsubstituted cyclic alkyl, substituted or unsubstituted aryl, substituted or unsubstituted heterocyclic aryl, or substituted or unsubstituted heterocyclic alkyl;

$R^2$, $R^3$, $R^4$, $R^5$ are individually a hydrogen, hydroxyl, azyl, nitryl, cyano group, halogen, alkyl, alkoxy, cycloalkyl, aryl, aryl alkyl, heterocyclic aryl or heterocyclic alkyl; and Ar is a substituted or unsubstituted heterocyclic aryl, excluding benzpyrrole.

Moreover, the present application relates to a method for suppressing IL-1β secretion of microglial cell, comprising making microglial cell contact with treatment effective dose of a compound represented by formula (I) or the pharmaceutical acceptable salt thereof:

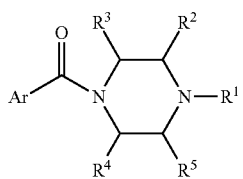

Formula I

Wherein, $R^1$ is a hydrogen, substituted or unsubstituted alkyl, substituted or unsubstituted cyclic alkyl, substituted or unsubstituted aryl, substituted or unsubstituted heterocyclic aryl, or substituted or unsubstituted heterocyclic alkyl;

$R^2$, $R^3$, $R^4$, $R^5$ are individually a hydrogen, hydroxyl, azyl, nitryl, cyano group, halogen, alkyl, alkoxy, cycloalkyl, aryl, aryl alkyl, heterocyclic aryl or heterocyclic alkyl; and Ar is a substituted or unsubstituted heterocyclic aryl group, excluding benzpyrrole.

In addition, a method for treating and preventing nerve inflammatory disease or morbid state mediated by IL-1β, comprising administrating an individual who needs the method the treatment effective dose of a compound represented by formula (I) or the pharmaceutical acceptable salt thereof

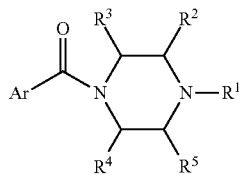

Formula I

Wherein, $R^1$ is a hydrogen, substituted or unsubstituted alkyl, substituted or unsubstituted cyclic alkyl, substituted or unsubstituted aryl, substituted or unsubstituted heterocyclic aryl, or substituted or unsubstituted heterocyclic alkyl;

$R^2$, $R^3$, $R^4$, $R^5$ are individually a hydrogen, hydroxyl, azyl, nitryl, cyano group, halogen, alkyl, alkoxy, cycloalkyl, aryl, aryl alkyl, heterocyclic aryl or heterocyclic alkyl; and Ar is a substituted or unsubstituted heterocyclic aryl, excluding benzpyrrole.

In other aspects, the present application relates to a method for treating and preventing Senile Dementia (Alzheimer's disease), comprising administrating the treatment effective dose of a compound represented by formula (I) or the pharmaceutical acceptable salt thereof to an individual who needs the method:

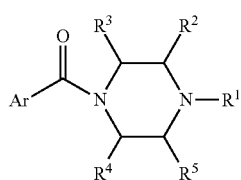

Formula (I)

wherein $R^1$ is a hydrogen, substituted or unsubstituted alkyl, substituted or unsubstituted cyclic alkyl, substituted or unsubstituted aryl, substituted or unsubstituted heterocyclic aryl, or substituted or unsubstituted heterocyclic alkyl;

$R^2$, $R^3$, $R^4$, $R^5$ are individually a hydrogen, hydroxyl, azyl, nitryl, cyano group, halogen, alkyl, alkoxy, cycloalkyl, aryl, aryl alkyl, heterocyclic aryl or heterocyclic alkyl; and Ar is a substituted or unsubstituted heterocyclic aryl.

DETAILS

Unless other requirement in the present application, in the whole specification and claims, word "comprise" and its English variants, for example "comprises" and "comprising" shall be explained to have the opening and consisting meaning, i.e. "include but not be limited within".

In the whole specification, "one embodiment" or "embodiment" or "in another embodiment" or "in some embodiments" means one embodiment comprising the specific elements, structures or features relative to the embodiment. Therefore, in the whole specification, the phrases "in one embodiment" or "during the embodiment" or "in another embodiment" showing up in different places do not mean one single embodiment. In addition, except conflicting with each other, mentioned specific elements, structures or features constituting an embodiment can be combined in a proper way in one or more than one embodiments.

It shall be understood that the articles in singular form "a", "an" and "the" in the specification and claims of the present application include plural objects, unless the explicit requirement in the application. Therefore, for example, "pharmaceutical acceptable carrier" as mentioned comprises one pharmaceutical acceptable carrier, or two or multiple pharmaceutical acceptable carriers. Furthery, it is understood that term "or" is usually used with the meaning of "and/or", unless the explicit requirement in the application.

DEFINITIONS

In shown chemical groups, the simplified symbol (for example $C_4$) of the total number of carbon atoms indicates some chemical groups named in the application. For example, $C_7$-$C_{12}$ alkyl describe the alkyl group with 7-12 carbon atoms as defined below, and $C_4$-$C_{12}$ cyclic alkyl describe the cyclic alkyl group with 4-12 carbon atoms as defined below. The number of carbon atoms in simplified symbol does not comprise carbon atom which may exist in substituent of the chemical group.

Therefore, unless the opposite explanation in the application, terms mentioned below which are used in the specification and claims have the meaning as followings:

Term of "halogen" refers to fluorine, chlorine, bromine and iodine.

Term of "alkyl" refers to saturated fat alkyl group of linear or branched chain which consists of carbon and hydrogen atoms, binding to other part of the molecule through a single bond. The alkyl group having 1-6 carbon atoms, the examples of alkyl group include but are not limited within methyl, ethyl, propyl, isopropyl, n-butyl, isobutyl or tert-butyl, pentyl, 2-methyl-butyl, neopentyl, n-hexyl etc. Alkyl group can be substituted or unsubstituted.

Term of "halogenated alkyl" refers to "alkyl" group substituted with one or more than one "halogen" atoms, including mono-halogeno alkyl, second bi-halogeno alky, tri-halogeno alkyl and perhalogeno alkyl, etc, and examples of halogenated alkyl include but are not limited within chloromethyl, dichloromethyl, difluoromethyl, trifluoromethyl, perfluoromethyl or 2,2-2-tri-fluoroethyl, etc.

Term of "alkoxy" refers to —O-alkyl group, and examples of alkoxy include but are not limited within methoxy, ethoxy, propoxy, isopropoxy, n-butoxy, iso-butoxy, tert-butoxy, n-pentyloxy, 2-methyl-butoxy, neopentoxy, n-hexoxy etc.

Term of "amino group" or "azyl" refers to —NH$_2$, —NH(alkyl) and —N(alkyl)$_2$. Examples of alkyl group include but are not limited within —NH$_2$, —NHCH$_3$, —N(CH$_3$)$_2$, —NHC$_{1-3}$ alkyl, —N(C$_{1-3}$ alkyl)$_2$ etc.

Term of "aryl" refers to carbon monocyclic with complete conjugate π electronic system or fused polycyclic aromatic ring group. In some embodiments, aryl groups have 6-14 carbon atoms. In some embodiments, aryl groups have 6-10 carbon atoms. In some embodiments, aryl groups have 6 carbon atoms. Examples of aryl groups include but are not limited within phenyl, naphthyl, anthryl etc.

Term of "$C_6$-$C_{10}$ aryl" refers to aryl groups with 6-10 carbon atoms as above defined. Term "aryl alkyl" refers to alkyl groups substituted with aryl group as above defined. Examples of aryl alkyl include but are not limited within —CH$_2$-phenyl, —(CH$_2$)$_2$-phenyl, —(CH$_2$)$_3$-phenyl, —CH$_2$—CH(CH$_3$)-phenyl, —(CH$_2$)$_4$-phenyl, —CH$_2$—CH(CH$_3$)—CH$_2$-phenyl, —CH$_2$—CH$_2$—CH(CH$_3$)-phenyl, etc.

Term of "$C_7$-$C_{20}$ aryl alkyl" refers to aryl groups with 7-20 carbon atoms as above defined.

Term of "heterocyclic aryl" refers to monocyclic or bicyclic aromatic ring groups with 5-10 atoms, wherein at least one is N, O or S heteroatom, the rest are C, with complete conjugated π electronic system. Examples of heterocyclic aryl groups include but are not limited within pyridazine, quinazoline, pyrrole, thiophene, indazole, parazole, quinoline, pyridine, furan, imidazole, pyrazine, pyrimidine, thiazole, isoquinoline, benzothiazole or naphthyridine etc. Heterocyclic aryl group can be substituted or unsubstituted.

Term of "cyclic alkyl" refers to saturated cyclic alkyl groups with 3-10 carbon atoms. Examples of cyclic alkyl groups include but are not limited within cyclopropyl, cyclobutyl, cyclopentyl, cyclohexyl, cycloheptyl, adamantly etc. cyclic alkyl group can be substituted or unsubstituted cycloalkyl.

Term of "heterocyclic alkyl" refers to saturated cyclic alkyl groups with 3-10 carbon atoms, wherein one atom is N, O or S heteroatom, the rest are C. In some embodiments, heterocyclic alkyl groups have 3-6 atoms. Example of heterocyclic alkyl group includes but is not limited to ioxolanyl.

Term of "substitution" or "substituted" refers to one or more than one hydrogen atoms of the group are individually replaced by the same or different substituents. Most common substituent examples include but are not limited within hydroxyl, azyl, nitryl, cyano group, halogen, alkyl, alkoxyl, cyclic akryl, aryl, aryl alkyl, heterocyclic aryl or heterocyclic alkyl etc.

Term of "pharmaceutical acceptable carriers" include but are not limited within any adjuvant, carrier, excipient, glidant, sweetener, diluent, preservative, dye/colorant, flavour enhancer, surfactant, wetting agent, dispersing agent, suspending agent, stabilizer, Isotonic agent, solvent or emulsifier etc. approved by FAD to be used for human or animal, and various forms of carriers have no side effect on pharmaceutical composition.

"Pharmaceutical acceptable salts" comprises "pharmaceutical acceptable acid addition salt" and "pharmaceutical acceptable base addition salt".

"Pharmaceutical acceptable acid addition salts" refer to salts which keep biological effectiveness and property of free base, and the acid addition salts are suitable in biological or other aspects and formed with inorganic acid or organic acid. The inorganic acids include but are not limited within hydrochloric acid, hydrobromic acid, sulfuric acid, nitric acid, phosphoric acid, etc., and the organic acids include but are not limited within acetic acid, 2,2-dichloroacetic acid, adipic acid, alginic acid, ascorbic acid, aspartic acid, benzenesulfonic acid, benzoic acid, 4-Acetamidobenzoic acid, camphanic acid, camphor-10-sulfonic acid, capric acid, caproic acid, octanoic acid, carbonic acid, cinnamic acid, citric acid, cyclohexansulfamic acid, dodecyl sulfuric acid, 1,2-ethanedisulfonicacid, ethanesulfonic acid, 2-hydroxy ethanesulfonic acid, formic acid, fumaric acid, galactaric acid, gentisic acid, glucoheptonic acid, gluconic acid, glucuronic acid, glutamic acid, glutaric acid, 2-oxopentanedioic acid, glycerophosphoric acid, glycollic acid, hippuric acid, isobutyric acid, lactic acid, lactobionic acid, lauric acid, maleic acid, malic acid, malonic acid, mandelic acid, methanesulfonic acid, mucic acid, 1.5-naphthalenedisulfonic acid, 2-naphthalenesulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, etc.

"Pharmaceutical acceptable base addition salts" refer to salts which keep biological effectiveness and property of free acid, and the base addition salts are suitable in biological or other aspects and formed by addition of inorganic base or organic base into free acid. The salts derived from inorganic base include but are not limited within sodium, potassium, lithium, ammonium, calcium, magnesium, ferrum, zinc, copper, manganese, aluminum salts etc. Preferably, inorganic salts are ammonium, sodium, potassium, calcium and manganese salts. The salts derived from inorganic base include but are not limited within primary, secondary and tertiary amine salts, substituted amine including naturally existing substituted amine, cyclamine and salt of alkaline ion exchange resin, for example, ammonia, isopropylamine, trimethyl amine, diethylamine, triethylamine, tripropylamine, diethanol amine, ethanol amine, N,N-dimethylethanolamine, 2-dimethylethanolamine, diethyl aminoethanol, dicyclohexylamine, lysine, arginine, histidine, caffeine, procaine, hydrabamine, choline, glycine betaine, benzylamine, phenylethylenediamine, ethylenediamine, glucosamine, methyl glucosamine, theobromine, triethanolamine, trometamol, purine, piperazine, piperidine, N-ethyl piperidine, Polyamine resin, etc. Preferably organic salts are isopropamide, diethylamine, trimethyl amine, dicyclohexylamine, choline and caffeine.

Term of "pharmaceutical composition" refers to preparation formed by compound of the present application with intermediates which are acceptable in the prior art and deliver the compound with biological activity to mammalian like human beings. The intermediates include all pharmaceutical acceptable carriers.

Term of "treatment effective dose" refers to the dose for effectively treating (defined as following) mammalian preferably human beings during drug administration, preferably dose for disease or morbid state mediated by IL-Iβ in human. According to compound, morbid state and severity thereof, and the age of the mammal needing the treatment, the treatment effective dose of the compound of the present application will be different, and the technical individual in the filed will determine the dose of the compound of the present application with common knowledge and the present disclosure.

"Treating" or "treat" in the present application covers mammals with relative disease or symptom, preferably, human beings with relative disease or morbid state, and comprises:

(i) Prevention of disease or morbid state happening in mammals, particularly when the mammal is susceptible to the morbid state, but has not been diagnosed having the morbid state;

(ii) Suppression of disease or morbid state, i.e. stopping them from happening; or (iii) Anesis of disease or morbid state, i.e. recession of disease or morbid state.

As used in a way as in the present application, terms of "disease" and "morbid state" can replace each other, or may be different, because some special diseases or morbid states do not have known pathogenic factors (so they can not be explained by nosetiology), therefore, they are not considered as diseases, instead of being some unexpected morbid states or symptoms, wherein clinician have diagnosed more or less symptoms of special series.

DETAILED DESCRIPTION OF THE PREFERRED EMBODIMENTS

On one hand, the present application relates to a compound represented by formula (I) and the pharmaceutical acceptable salt thereof:

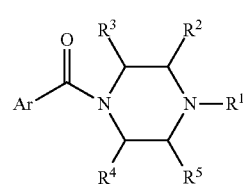

Formula (I)

wherein, $R^1$ is a hydrogen, substituted or unsubstituted alkyl, substituted or unsubstituted cyclic alkyl, substituted or unsubstituted aryl, substituted or unsubstituted heterocyclic aryl, or substituted or unsubstituted heterocyclic alkyl;

$R^2$, $R^3$, $R^4$, $R^5$ are selected from the group consisting of hydrogen, hydroxyl, azyl, nitryl, cyano group, halogen, alkyl, alkoxy, cycloalkyl, aryl, aryl alkyl, heterocyclic aryl and heterocyclic alkyl, respectively; and Ar is a substituted or unsubstituted heterocyclic aryl, excluding benzpyrrole.

In some embodiments, substituent of $R^1$ is an aryl, aryl alkyl, alkoxy, halogenated alkyl, halogen, hydroxyl, azyl or cyano group.

In some embodiments, substituent of Ar is an alkyl, alkoxy, halogenated alkyl, halogen, nitryl, hydroxyl, azyl, aryl, aryl alkyl or aryloxy.

On the other hand, pharmaceutical acceptable salt:

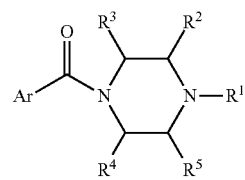

Formula (I)

Wherein, $R^1$ is a hydrogen, substituted or unsubstituted alkyl, substituted or unsubstituted cyclic alkyl, substituted or unsubstituted aryl, substituted or unsubstituted heterocyclic aryl, or substituted or unsubstituted heterocyclic alkyl, wherein substituents thereof are selected from the group consisting of aryl, aryl alkyl, alkyl, alkoxy, substituted alkyl, halogen, hydroxyl, azyl and cyano group, respectively;

$R^2$, $R^3$, $R^4$, $R^5$ are individually a hydrogen, hydroxyl, azyl, nitryl, cyano group, halogen, alkyl, alkoxy, cycloalkyl, aryl, aryl alkyl, heterocyclic aryl or heterocyclic alkyl; and Ar is a substituted or unsubstituted heterocyclic aryl group, excluding benzpyrrole, wherein substituent is an alkyl, alkoxy, Halogenated alkyl, halogen, hydroxyl, azyl, aryl, aryl alkyl or aryloxy.

In some embodiments, alkyl is $C_1$-$C_6$ alkyl group.

In some embodiments, cyclic alkyl is $C_3$-$C_{10}$ cyclic alkyl group.

In some embodiments, aryl is $C_6$-$C_{10}$ aryl group.

In some embodiments, heterocyclic aryl is heterocyclic aryl group with 5 to 10 atoms.

In some embodiments, heterocyclic alkyl is heterocyclic alkyl with 3 to 10 atoms, 3 to 8 atoms or 3 to 6 atoms.

In some embodiments, $R^1$ is substituted or unsubstituted $C_1$-$C_6$ alkyl, $C_3$-$C_{10}$ substituted or unsubstituted cyclic alkyl, substituted or unsubstituted phenyl, substituted or unsubstituted pyrimidyl, substituted or unsubstituted pyridyl, substituted or unsubstituted pyrazinyl, wherein substituent is an aryl, aryl alkyl, alkyl, alkoxy, halogenated alkyl, halogen, hydroxyl, azyl or cyano group.

In some embodiments, $R^1$ is substituted or unsubstituted $C_1$-$C_6$ alkyl, substituted or unsubstituted $C_3$-$C_{10}$ cyclic alkyl, substituted or unsubstituted phenyl, substituted or unsubstituted pyrimidyl, substituted or unsubstituted pyridyl, substituted or unsubstituted pyrazinyl, wherein substituent is an aryl, aryl alkyl, alkyl, alkoxy, halogenated alkyl, halogen, hydroxyl, azyl or cyano group.

In some embodiments, $R^1$ is substituted or unsubstituted $C_1$-$C_6$ alkyl, substituted or unsubstituted $C_3$-$C_{10}$ cyclic alkyl, substituted or unsubstituted phenyl, substituted or unsubstituted pyrimidyl, substituted or unsubstituted pyridyl, substituted or unsubstituted pyrazinyl, wherein substituent is a methyl, ethyl, fluorine, chlorine, bromine, hydroxyl, methoxy, or trifluoromethyl.

In some embodiments, $R^1$ is a phenyl, 4-fluorophenyl, 2,4-difluorophenyl, 2-fluorophenyl, 4-chlorophenyl, 3-chlorophenyl, 4-bromophenyl, 4-hydroxyphenyl, 4-methylphenyl, 2-methoxyphenyl, 3-methoxyphenyl, 4-methoxyphenyl, 2-ethyl-4-fluorophenyl, 3-trifluoromethylphenyl, 2,3-difluorophenyl, 2-chloro-6-fluorophenyl, 3,4-dimethylphenyl, 3,4-dimethoxyphenyl, pyrimid-2-yl, 5-fluoropyrimid-2-yl, 5-bromoopyrimid-2-yl, pyridin-2-yl, pyridin-4-yl, 5-methylpyridin-2-yl, 3-trifluoromethylpyridin-2-yl, 5-trifluoromethylpyridin-2-yl, or 3-fluoro-5-trifluoromethylpyridin-2-yl, pyrazin-2-yl, methyl, isopropyl or cyclohexyl.

In some embodiments, $R^1$ is a 4-fluorophenyl, 2,4-difluorophenyl, pyrimid-2-yl, pyridin-2-yl, 5-fluoropyrimid-2-yl, pyrazin-2-yl, pyrazin-4-yl, methyl, isopropyl or cyclohexyl.

In some embodiments, $R^2$, $R^3$, $R^4$, $R^5$ is respectively selected from hydrogen, alkyl, alkoxy, phenyl or phenyl alkyl.

In some embodiments, $R^2$, $R^3$, $R^4$, $R^5$ is selected from hydrogen.

In some embodiments, Ar is a substituted or unsubstituted pyridazinyl, substituted or unsubstituted quinazolinyl, substituted or unsubstituted pyrrolyl, substituted or unsubstituted thienyl, substituted or unsubstituted indazolyl or substituted or unsubstituted pyrazolyl.

In some embodiments, Ar is a substituted or unsubstituted pyridazinyl, wherein substituent is a methyl, methoxy, halogenated alkyl, halogen, azyl or aryl.

In some embodiments, Ar is a substituted or unsubstituted pyridazinyl, wherein substituent is a methyl, phenyl, methoxy, trifluoromethyl, azyl or chlorine.

In some embodiments, Ar is a 4-methyl-6-phenylpyridazin-3-yl, 6-phenylpyridazin-3-yl, 6-methylpyridazin-3-yl, 6-methoxylpyridazin-3-yl, 6-trifluoromethylpyridazin-3-yl, 6-trifluoro methylpyridazin-3-yl, 6-aminopyridazin-3-yl, 6-fluoropyridazin-3-yl, pyridazin-4-yl, 2-phenylquinazolin-4-yl, quinazolin-4-yl, 2-trifluoromethylquinazolin-4-yl, 7-methoxyquinazolin-4-yl, pyrrol-2-yl, pyrrol-3-yl, 4-methylpyrrol-2-yl, 1-phenylpyrrol-3-yl, 2,4-dimethylpyrrol-3-yl, 3,5-dimethylpyrrol-2-yl, thien-3-yl, thien-2-yl, 5-nitrylthien-2-yl, 5-methylthien-2-yl, 4-methylthien-2-yl, 4-chlorothien-2-yl, 3-bromothien-2-yl, 3-aminothien-2-yl, 3-amino-4-methylthien-2-yl, 4,5-dimethyl-4-methylthien-2-yl, indazol-3-yl, 5-fluoroindazol-3-yl, 5-chloroindazol-3-yl, 4,7-dichloroindazol-3-yl, 6-methoxyindazol-3-yl, 4-methoxyindazol-3-yl, 5-methoxyindazol-3-yl, 1-methylindazol-3-yl, 5-methylindazol-3-yl, 7-chloroindazol-3-yl, 5-nitrylindazol-3-yl, 5,6-dichloroindazol-3-yl, pyrazol-3-yl, 5-isopropyl pyrazol-3-yl, 3-amniopyrazol-4-yl, 1-methyl-4-chloropyrazol-3-yl, 5-nitryl-1-methylpyrazol-3-yl, or 1-methyl-5-amino-pyrazol-4-yl.

In some embodiments, Ar is a 4-methyl-6-phenylpyridazin-3-yl, 2-phenylquinazolin-4-yl, pyrrol-2-yl, pyrrol-2-yl, indazol-3-yl, 5-fluoroindazol-3-yl, 4,7-difluoroindazol-3-yl, 5-chloroindazol-3-yl, 5-isopropylindazol-3-yl.

In some embodiments, $R^1$ is a hydrogen, substituted or unsubstituted alkyl, substituted or unsubstituted cyclic alkyl, substituted or unsubstituted aryl, or substituted or unsubstituted heterocyclic alkyl, wherein substituent is an aryl, aryl alkyl, alkyl, alkoxy, substituted alkyl, halogen, hydroxyl, azyl, or cyano group; $R^2$, $R^3$, $R^4$, $R^5$ are individually a hydrogen, hydroxyl, azyl, nitryl, cyano group, halogen, alkyl, alkoxy, cycloalkyl, aryl, aryl alkyl, heterocyclic aryl or heterocyclic alkyl; and Ar is a substituted or unsubstituted pyridazinyl, substituted or unsubstituted quinazolinyl, substituted or unsubstituted pyrrolyl, substituted or unsubstituted thienyl, substituted or unsubstituted indazolyl, substituted or unsubstituted pyrazolyl, wherein substituent is an alkyl, alkoxy, halogenated alkyl, halogen, hydroxyl, azyl, aryl, aryl alkyl or aryloxy.

In some embodiments, $R^1$ is an substituted or unsubstituted alkyl, substituted or unsubstituted cyclic alkyl, substituted or unsubstituted aryl, or substituted or unsubstituted heterocyclic alkyl, wherein substituent is an aryl, aryl alkyl, alkyl, alkoxy, substituted alkyl, halogen, hydroxyl, azyl, or cyano group; $R^2$, $R^3$, $R^4$, $R^5$ are individually hydrogen; and Ar is a substituted or unsubstituted pyridazinyl, substituted or unsubstituted quinazolinyl, substituted or unsubstituted pyrrolyl, substituted or unsubstituted thienyl, substituted or unsubstituted indazolyl, 1 substituted or unsubstituted pyrazoly, wherein substituent is an alkyl, alkoxy, halogenated alkyl, halogen, hydroxyl, azyl, aryl, aryl alkyl or aryloxy.

In some embodiments, $R^1$ is an substituted or unsubstituted alkyl, substituted or unsubstituted cyclic alkyl, substituted or unsubstituted phenyl, substituted or unsubstituted pyrimidyl, substituted or unsubstituted pyridyl, substituted or unsubstituted pyrazinyl, wherein substituent is an aryl, aryl alkyl, alkyl, alkoxy, substituted alkyl, halogen, hydroxyl, azyl, or cyano group; $R^2$, $R^3$, $R^4$, $R^5$ are individually hydrogen; Ar is a substituted or unsubstituted pyridazinyl, wherein substituent is an alkyl, alkoxy, halogenated alkyl, halogen, hydroxyl, azyl, or aryl.

In some embodiments, $R^1$ is a substituted or unsubstituted alkyl, substituted or unsubstituted cyclic alkyl, substituted or unsubstituted phenyl, substituted or unsubstituted pyrimidyl, substituted or unsubstituted pyridyl, substituted or unsubstituted pyrazinyl, wherein substituent is a methyl, ethyl, fluorine, chlorine, bromine, hydroxyl, methoxy or trifluoromethyl; $R^2$, $R^3$, $R^4$, $R^5$ are individually hydrogen; Ar is a substituted or unsubstituted pyridazinyl, wherein substituent is a methyl, phenyl, methoxy, trifluoromethyl, azyl or chorine.

In some embodiments, a compound represented by formula (I) or the pharmaceutical acceptable salt thereof is:
(4-(4-fluorophenyl) piperazinyl) (4-methyl-6-phenylpyridazinyl) ketone;
(4-(2,4-difluorophenyl)piperazinyl)(4-methyl-6-phenylpyridazinyl) ketone;
(2-Pyrimidylpiperazinyl) (4-methyl-6-phenylpyridazinyl) ketone;
(2-Pyridinylpiperazinyl) (4-methyl-6-phenylpyridazinyl) ketone;
(4-(4-fluorophenyl) piperazinyl) (2-phenylquinazolinyl) ketone;
(4-(5-fluoropyrimid-2-yl) piperazinyl)(2-phenylquinazolinyl) ketone;
(4-(Pyrimid-2-yl) piperazinyl)(2-phenylquinazolinyl)ketone;
(4-(2-Pyridinyl) piperazinyl)(2-phenylquinazolinyl) ketone;
(4-(4-fluorophenyl) piperazinyl) (pyrrol-2-yl) ketone;
(4-(4-fluorophenyl) piperazinyl) (thien-2-yl) ketone;
(4-(Pyrimid-2-yl) piperazinyl) (indazol-3-yl) ketone;

(4-(4-fluorophenyl) piperazinyl) (indazol-3-yl) ketone;
(4-(4-fluorophenyl) piperazinyl) (5-fluoroindazol-3-yl) ketone;
(4-(4-fluorophenyl) piperazinyl) (4,7-difluoroindazol-3-yl) ketone;
(4-(4-fluorophenyl) piperazinyl) (5-fluoroindazol-3-yl) ketone;
(4-(2-Pyrimidyl) piperazinyl) (5-isopropylpyrazol-3-yl) ketone;
(4-(4-fluorophenyl) piperazinyl) (5-isopropylpyrazol-3-yl) ketone;
(2-(4-fluoropyrimidyl) piperazinyl) (4-methyl-6-phenylpyridazinyl) ketone;
(2-pyrazinylpiperazinyl) (4-methyl-6-phenylpyridazinyl) ketone;
(N-methylpiperazinyl) (4-methyl-6-phenylpyridazinyl) ketone;
(N-isopropylpiperazinyl) (4-methyl-6-phenylpyridazinyl) ketone;
(N-cyclohexylpiperazinyl) (4-methyl-6-phenylpyridazinyl) ketone;
(4-(4-pyridinyl)piperazinyl) (2-phenylquinazolinyl)ketone;
(4-(2-pyrazinyl) piperazinyl) (2-phenylquinazolinyl) ketone;
(4-methylpiperazinyl) (2-phenylquinazolinyl) ketone;
(4-isopropylpiperazinyl) (2-phenylquinazolinyl) ketone; or
(cyclohexylpiperazinyl) (2-phenylquinazolinyl) ketone.

On the other hand, the present application relates to a method for preparing a compound and the pharmaceutical acceptable salt thereof, comprising the reaction of a compound represented by formula (A) and a compound represented by formula (B):

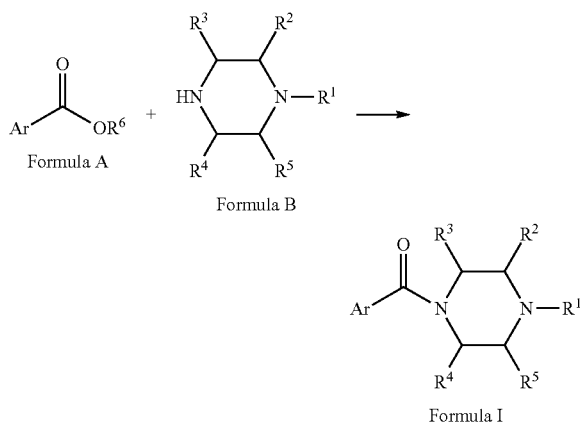

Wherein $R^1$ is a hydrogen, substituted or unsubstituted alkyl, substituted or unsubstituted cyclic alkyl, substituted or unsubstituted aryl, substituted or unsubstituted heterocyclic aryl, or substituted or unsubstituted heterocyclic alkyl;

$R^2$, $R^3$, $R^4$, $R^5$ are individually a hydrogen, hydroxyl, azyl, nitryl, cyano group, halogen, alkyl, alkoxy, cycloalkyl, aryl, aryl alkyl, heterocyclic aryl or heterocyclic alkyl; and Ar is a substituted or unsubstituted heterocyclic aryl, excluding benzpyrrole; and $R^6$ is a hydrogen or alkyl.

In some embodiments, substituents of $R^1$ are selected from aryl, aryl alkyl, alkyl, alkoxy, substituted alkyl, halogen, hydroxyl, azyl, or cyano group, respectively.

In some embodiments, a substituent of Ar is an alkyl, alkoxy, halogenated alkyl, halogen, hydroxyl, azyl, aryl, aryl alkyl or aryloxy.

In some embodiments, the embodiments comprise: in organic solvent, in presence of condensating agent, a compound represented by formula (I) and the salt thereof are formed with the reaction of a compound represented by formula (A) and a compound represented by formula (B).

Condensating agent is N,N-dicyclohexylcarbodiimide (DCC),
N,N-diisopropylcarbodiimide (DIC), N-(ethylcarbonimidoyl)-N,N-dimethylpropane-1,3-diamine (EDC) or 1-ethyl-(3-dimethylaminopropyl)carbodiimide hydrochloride (EDCI). Organic solvent is dichloromethane or tetrahydrofuran.

In some embodiments, mix a compound represented by formula (A) and a compound represented by formula (B), add dichloromethane or tetrahydrofuran, and furtherly add the condensating agent, following by extraction with dichloromethane. The organic phase is dried by anhydrous sodium sulfate, and a compound represented by formula (I) is obtained after concentration and column chromatography.

In some embodiments, while Ar is a substituted or unsubstituted pyridazinyl group, or substituted or unsubstituted quinazolinyl group, while $R^6$ is hydrogen,

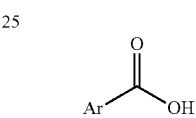

can be synthesized in a method as following:

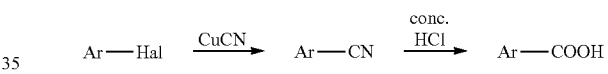

wherein, Hal represents halogen, for example, chlorine, bromine, iodine etc., and raw material Ar-Hal can be bought from market, or be prepared according to the methods disclosed by applications of WO 2008/023357 or WO 2007/127375.

Mix a pyridazine substituted or unsubstituted or quinazoline halide substituted or unsubstituted (Ar-Hal) with cuprous cyanide or potassium cyanide, to conduct the reaction.

In some embodiments, add pyridine or N,N-dimethylformamide, and the mixture reacts for 2-48 hours under 60°-160° C., after filtration, add dilute hydrochloric acid and extract with ethyl acetate. The organic phase is dried by anhydrous sodium sulfate, and after concentration the raw product is heated in 6-10M hydrochloric acid, following by 3-8 hours reflusing, and is neutralized with saturated sodium carbonate solution, and then extract with ethyl acetate. The aqueous phase is adjusted to pH2 with dilute hydrochloric acid, extracted with ethyl acetate, dried with anhydrous sodium sulfate, and obtain the raw product after concentration In some embodiments, the mole ratio of pyridazine substituted or unsubstituted or quinazoline halide substituted or unsubstituted to cuprous cyanide is 1:1.0-2.0, preferably, 1:1.8, more particularly, 1:1.5; the reaction time is 2-48 hours, preferably 24 hours, more particularly, 2 hours; reaction temperature is 60-160° C., preferably 130° C., more particularly, 80° C.

Furtherly, the present application relates to a pharmaceutical composition, comprising treatment effective dose of a compound represented by formula (I)

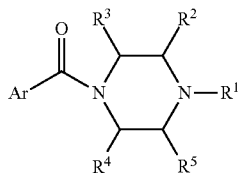

Formula (I)

wherein, $R^1$ is a hydrogen, substituted or unsubstituted alkyl, substituted or unsubstituted cyclic alkyl, substituted or unsubstituted aryl, substituted or unsubstituted heterocyclic aryl, or substituted or unsubstituted heterocyclic alkyl;

$R^2$, $R^3$, $R^4$, $R^5$ are individually a hydrogen, hydroxyl, azyl, nitryl, cyano group, halogen, alkyl, alkoxy, cycloalkyl, aryl, aryl alkyl, heterocyclic aryl or heterocyclic alkyl; and Ar is a substituted or unsubstituted heterocyclic aryl group, excluding benzpyrrole. In some embodiments, substituent of $R^1$ is an aryl, aryl alkyl, alkoxy, halogenated alkyl, halogen, hydroxyl, azyl or cyano group.

In some embodiments, substituent of Ar is an alkyl, alkoxy, halogenated alkyl, halogen, hydroxyl, azyl, aryl, aryl alkyl or aryloxy.

In some embodiments, a pharmaceutical composition of the present application can be a liquid, half liquid or solid state.

Examples of pharmaceutical acceptable carriers applicable in the pharmaceutical composition of the present application, include but are not limited within any adjuvant, carrier, excipient, glidant, sweetener, diluent, preservative, dye/colorant, flavour enhancer, surfactant, wetting agent, dispersing agent, suspending agent, stabilizer, isotonic agent, solvent or emulsifier etc. approved by FAD to be used to human or animal, various forms of which have no side effect on pharmaceutical composition.

In some embodiments, the pharmaceutical composition of the present application is prepared as tablet, solution, granule, patch, oint, capsule, aerosol, or suppository used through parenteral, percutaneous, mucous membrane, nosal, buccal, hypogloeeis or oral administration.

Oral pharmaceutical composition can be solid, gel or liquid. Examples of solid preparation include but are not limited within tablet, capsule, granule and bulk powder. These preparations can selectively comprise adhesion agent, diluent, disintegrant, lubricant, glidant, sweetener, corrective flavoring agents, etc. Examples of adhesion agents include but are not limited within microcrystalline cellulose, glucose solution, acacia mucilage, gelatin solution, sucrose and starch paste; examples of lubricants include but are not limited within talc, starch, magnesium stearate, calcium stearate, stearic acid; examples of diluents include but are not limited within lactose, sucrose, starch, mannitol, dicalcium phosphate; examples of glidant comprise but are not limited within silicon dioxide; examples of disintegrating agent include but are not limited within croscarmellose sodium, carboxyethylstach sodium, alginic acid, corn starch, potato starch, methyl cellulose, agar and carboxymethyl cellulose.

The pharmaceutical composition of the present application by parenteral administration, majorly uses medical injection, comprising subcutaneous, intramuscular or intravenous injections. Injection can be prepared in any conventional form, for example, liquid solution or suspension solution, solid form or emulsion which can be dissolved or resuspended in liquid before injection. Examples of pharmaceutical acceptable carriers applicable in the injection of the present application include but are not limited within hydrophilic carrier, hydrophobic carrier, antimicrobial, Isotonic agent, buffer agent, antioxidant, suspension and dispersant, emulsifying agent, chelating agent, other pharmaceutical acceptable materials. Examples of hydrophilic carrier comprise sodium chloride injection solution, Ringer's injection, isotonic glucose injection, sterile water injection, glucose and lactated Ringer's Injection; examples of hydrophobic carrier include fixed oil from plant, cottonseed oil, corn oil, sesame oil and peanut oil; Examples of antimicrobial comprise cresol, benzyl alcohol, chlorobutanol, benzalkonium chloride etc.; examples of isotonic agents comprise sodium chloride and glucose; examples of buffer agent comprise phosphate and citrate.

The pharmaceutical composition of the present application can be prepared as sterile freeze-dried powder injection, dissolve compounds into sodium phosphate buffer, which also comprises glucose or other proper excipients, then, an individual with general technical knowledge in the prior art sterile the solution by filtration under known standard conditions, following by lyophilization to obtain the needed preparation.

In addition, the present application relates to a method suppressing IL-1β secretion of microglial cell, comprising making microglial cell contact with treatment effective dose of a compound represented by formula (I) or the pharmaceutical acceptable salt thereof:

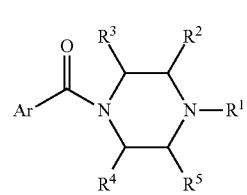

Formula (I)

Wherein $R^1$ is a hydrogen, substituted or unsubstituted alkyl, substituted or unsubstituted cyclic alkyl, substituted or unsubstituted aryl, substituted or unsubstituted heterocyclic aryl, or substituted or unsubstituted heterocyclic alkyl;

$R^2$, $R^3$, $R^4$, $R^5$ are individually a hydrogen, hydroxyl, azyl, nitryl, cyano group, halogen, alkyl, alkoxy, cycloalkyl, aryl, aryl alkyl, heterocyclic aryl or heterocyclic alkyl; and Ar is a substituted or unsubstituted heterocyclic aryl group, excluding benzpyrrole.

In some embodiments, substituents of $R^1$ is an aryl, aryl alkyl, alkyl, alkoxy, substituted alkyl, halogen, hydroxyl, azyl, or cyano group.

In some embodiments, substituent of Ar is alkyl, alkoxy, halogenated alkyl, halogen, hydroxyl, azyl, aryl, aryl alkyl or aryloxy.

Additionally, the present application relates to a method for treating and preventing nerve inflammatory disease or morbid state mediated by IL-4β, comprising administrating the treatment effective dose of a compound represented by formula (I) or the pharmaceutical acceptable salt thereof to an individual who needs the method:

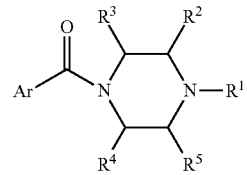

Formula (I)

Wherein R¹ is a hydrogen, substituted or unsubstituted alkyl, substituted or unsubstituted cyclic alkyl, substituted or unsubstituted aryl, substituted or unsubstituted heterocyclic aryl, or substituted or unsubstituted heterocyclic alkyl;

$R^2$, $R^3$, $R^4$, $R^5$ are individually a hydrogen, hydroxyl, azyl, nitryl, cyano group, halogen, alkyl, alkoxy, cycloalkyl, aryl, aryl alkyl, heterocyclic aryl or heterocyclic alkyl; and Ar is a substituted or unsubstituted heterocyclic aryl group, excluding benzpyrrole.

In some embodiments, substituent of R¹ is aryl, aryl alkyl, alkyl, alkoxy, substituted alkyl, halogen, hydroxyl, azyl, or cyano group.

In some embodiments, substituent of Ar is alkyl, alkoxy, halogenated alkyl, halogen, hydroxyl, azyl, aryl, aryl alkyl or aryloxy.

In some embodiments, the disease or morbid state is Senile Dementia (Alzheimer's disease), Parkinson's disease, amyotrophic lateral sclerosis, autoimmune disease, prion disease apoplexy, traumatic brain injury, spinal muscular atrophy, disseminated sclerosis, epilepsy, and neuropathic pain.

In some embodiments, the compound represented by formula (I) or the pharmaceutical composition comprising a compound represented by formula (I) of the present application can be administered in the following administration ways: oral administration, parenteral administration, intraperitoneal administration, intravenous administration, transdermal administration, hypogloeeis administration, intramuscular administration, rectum administration, mouth, intranasal, liposomal administration, etc.

In other aspects, the present application relates to a method for treating and preventing Senile Dementia (Alzheimer's disease), comprising administrating the treatment effective dose of a compound represented by formula (I) or the pharmaceutical acceptable salt thereof to an individual who needs the method:

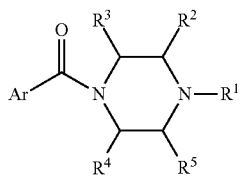

Formula (I)

wherein R¹ is a hydrogen, substituted or unsubstituted alkyl, substituted or unsubstituted cyclic alkyl, substituted or unsubstituted aryl, substituted or unsubstituted heterocyclic aryl, or substituted or unsubstituted heterocyclic alkyl;

$R^2$, $R^3$, $R^4$, $R^5$ are individually a hydrogen, hydroxyl, azyl, nitryl, cyano group, halogen, alkyl, alkoxy, cycloalkyl, aryl, aryl alkyl, heterocyclic aryl or heterocyclic alkyl; and Ar is a heterocyclic aryl group substituted or unsubstituted, excluding benzpyrrole.

In some embodiments, substituent of R¹ is an aryl, aryl alkyl, alkyl, alkoxy, substituted alkyl, halogen, hydroxyl, azyl, or cyano group In some embodiments, substituent of Ar is an alkyl, alkoxy, halogenated alkyl, halogen, hydroxyl, azyl, aryl, aryl alkyl or aryloxy.

Embodiments

Although any individual with general technical knowledge in the prior art can prepare the compound of the present application according to the above disclosure, the specification provides more detailed synthesis technique for preparing the compound of the present invention for convenience. Additionally, all reagents and reaction conditions used by the individual with general technical knowledge in the prior art in the known synthesis can be obtained from ordinary commodity.

The starting material 3-chloro-4-methyl-6-phenylpyridazine in the specific embodiments of the present application can be synthesized according to the disclose of the international application WO 2007/127375, and 4-chloro-2-phenyl quinazoline can be synthesized according to the disclosure of the international application WO 2008/023357, and all contents of above mentioned application are introduced in the present application as reference. Other starting materials or reaction reagents are all commercial available products, unless special requirement.

Nuclear magnetic resonance spectrometer (400 MHz) AV400, in the embodiments of the present application is made by Bruker Company (Switzerland).

Embodiment 1

(4-(4-fluorophenyl) piperazinyl) (4-methyl-6-phenylpyridazinyl) ketone (Compound 4)

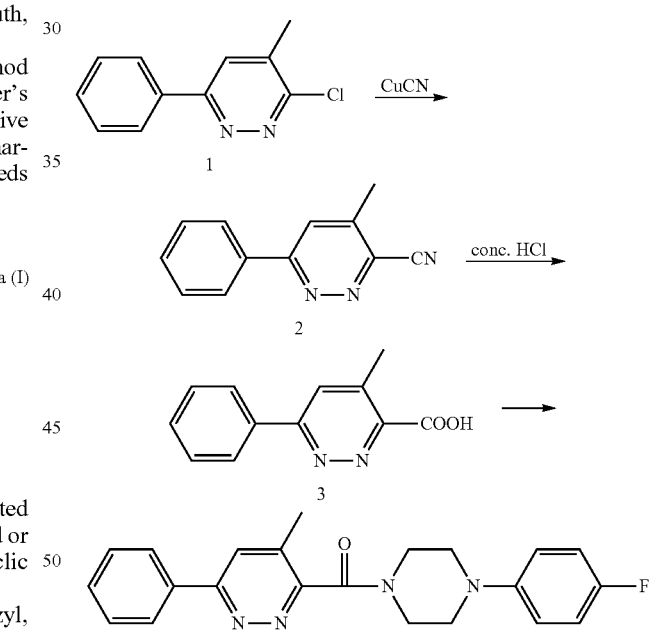

(1) 3-cyan-4-methyl-6-phenyl pyridazine (compound 2)

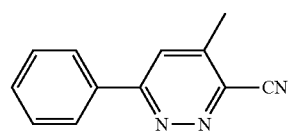

Add 1.25 g (6.1 mol) 3-chloro-4-methyl-6-phenyl pyridazine, 0.99 g (11.0 mol) cuprous cyanide and 20 mL pyridine into 50 mL pressure reaction tube, allow the mixture react for 24 hours at 130° C. then cool down and filtrate, and wash the cake three times with 50 mL ethyl acetate, and the organic phase is washed twice with 100 mL 1N HCl, following by drying with anhydrous sodium sulfate, and brown solid compound, crude product 2, is obtained after concentration, the crude product can be directly used in the next step reaction without further purification, MS: 196.0 (M+H$^+$).

(2) 3-carboxyl-4-methyl-6-phenyl pyridazine (compound 3)

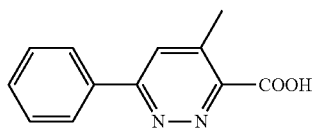

Add compound 2 prepared by Embodiment 1 into 20 mL 8 N HCl solution, heat and reflux for 4 hours, and after cooling down, add saturated sodium bicarbonate to neutralize the solution to obtain sodium salt, furtherly, extract twice with ethyl acetate, and water phase is adjusted to pH2 with dilute hydrochloric acid, and furtherly extract three times with ethyl acetate, following by drying with anhydrous sodium sulphate, and 0.59 g pale yellowish solid compound 3 after concentration, with yield of 55%, MS: 213.0 (M−H$^+$).

(3) Target Compound (Compound 4)

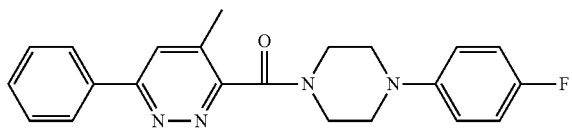

Add 0.40 g (1.87 mol) compound 3 and 20 mL dry dichloromethane to 50 mL round bottom flask, following by adding 0.30 g (2.24 mol) HOBt, 0.43 g (2.24 mol) EDC hydrochloride, 0.23 g triethylamine and 0.34 g (1.87 mol) 1-(4-fluorophenyl) piperazine. Stir the mixture for 18 hours at room temperature, then remove the dichloromethane by rotary evaporation, obtained oil product is extracted with 100 mL ethyl acetate and 50 mL saturated sodium bicarbonate, and the organic phase is dried by anhydrous sodium sulphate, 0.49 g white solid compound 4 is obtained after concentration and column chromatography with yield of 69%.

$^1$H-NMR (400 MHz, CDCl$_3$) δ 8.10-8.12 (m, 2H), 7.77 (s, 2H), 7.53-7.57 (m, 3H), 6.97-7.01 (m, 2H), 6.89-6.93 (m, 2H), 4.06 (t, J=4.8 Hz, 2H), 3.59 (t, J=4.8 Hz, 2H), 3.14 (t, J=4.8 Hz, 2H), 2.49 (s, 3H); MS: 377.2 (M+H$^+$).

Embodiment 2

(4-(2,4-difluorophenyl) piperazinyl) (4-methyl-6-phenylpyridazinyl) ketone (compound 4a)

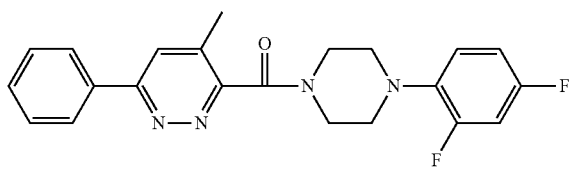

Use 1-(2,4-difluorophenyl)piperazine and 3-carboxyl-4-methyl-6-phenyl pyridazine as starting material, compound 4a is synthesized according to synthesis method of Compound 4 in Embodiment 1.

$^1$H-NMR (400 MHz, CDCl$_3$) δ 8.08-8.09 (m, 2H), 7.76 (s, 1H), 7.51-7.55 (m, 3H), 6.91-6.93 (m, 1H), 6.81-6.85 (m, 2H), 4.06 (t, J=4.8 Hz, 2H), 3.58 (t, J=4.8 Hz, 2H), 3.17 (t, J=4.8 Hz, 2H), 3.07 (t, J=4.8 Hz, 2H), 2.48 (s, 3H); MS: 395.1 (M+H$^+$), 417.1 (M+Na$^+$).

Embodiment 3

(2-pyrimidylpiperazinyl)(4-methyl-6-phenylpyridazinyl)ketone (compound 5)

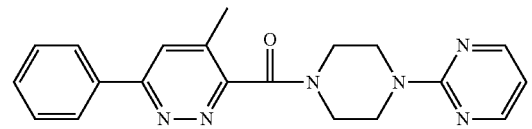

Use 1-(2-pyrimidinyl) piperazine and 3-carboxyl-4-methyl-6-phenyl pyridazine as starting material, compound 5 is synthesized according to synthesis method of Compound 4 in Embodiment 1.

$^1$H-NMR (400 MHz, CDCl$_3$) δ 8.32 (d, J=4.4 Hz, 2H), 8.08-8.11 (m, 2H), 7.77 (s, 1H), 7.51-7.54 (m, 3H), 6.54 (t, J=4.8 Hz, 1H), 4.03 (m, 2H), 3.97 (m, 2H), 3.90 (m, 2H), 3.50 (m, 2H), 2.48 (s, 3H); MS: m/e 361.1 (M+H$^+$), 383.1 (M+Na$^+$).

Embodiment 4

(2-pyridinylpiperazinyl) (4-methyl-6-phenylpyridazinyl) ketone (compound 6)

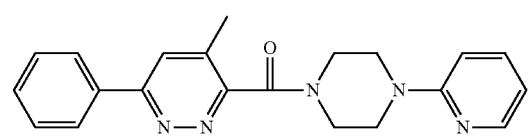

Use 1-(2-pyridyl) piperazine and 3-carboxyl-4-methyl-6-phenyl pyridazine as starting material, yellowish solid compound 6 is synthesized with yield of 64% according to synthesis method of Compound 4 in Embodiment 1.

$^1$H-NMR (400 MHz, CDCl$_3$) δ 8.19 (d, J=1.2 Hz, 2H), 8.08-8.11 (m, 2H), 7.76 (s, 1H), 7.49-7.56 (m, 4H), 6.68 (m, 1H), 4.02 (m, 2H), 3.74 (m, 2H), 3.63 (m, 2H), 3.55 (m, 2H), 2.48 (s, 3H). MS: m/e 360.1 (M+H$^+$), 382.1 (M+Na$^+$).

Embodiment 5

(4-(4-fluorophenyl) piperazinyl) (2-phenylquinazolinyl) ketone (Compound 11)

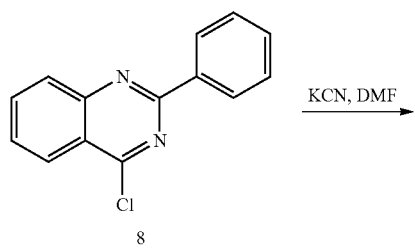

8

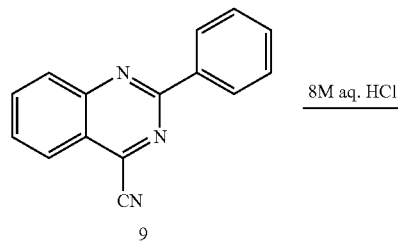

9

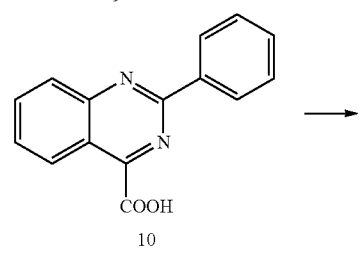

10

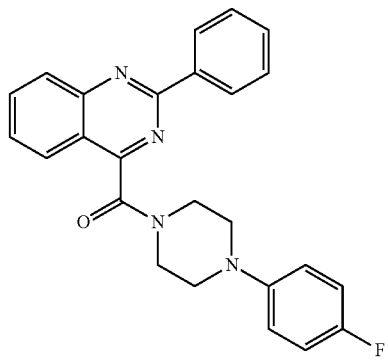

11

4-cyan-2-phenylquinazoline (Compound 9)

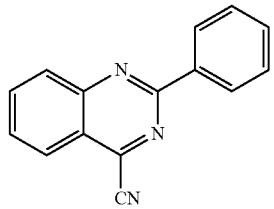

9

Add 1.00 g (4.15 mol) 4-chloro-2-phenylquinazoline, 0.40 g (6.23 mol) potassium cyanide, 0.27 g (1.38 mol) sodium p-toluenesulfonate and 20 mL N,N-dimethylformamide into 48 mL reaction tube, and allow the mixture react for 2 hours at 80° C., after cooling, add 50 mL and stir, then extract with 150 mL diethyl ether. The organic phase is dried with anhydrous sodium sulfate, and brown solid crude product compound 9 is obtained after concentration, MS: 232.0 (M+H$^+$).

(2) 2-phenyl-4-quinazoline-carboxylic acid

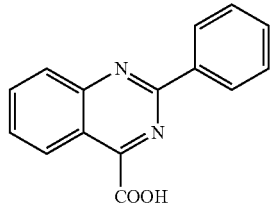

10

Add compound 9 and 20 mL 8 mol/L HCl solution to 50 mL round bottom flask, heat and reflux for 4 hours, and after cooling down, add saturated sodium bicarbonate to neutralize the solution to obtain sodium salt, furtherly, extract twice with ethyl acetate, and water phase is adjusted to pH2 with dilute hydrochloric acid, and furtherly extract three times with ethyl acetate, following by drying with anhydrous sodium sulphate, and 0.75 g pale yellowish solid compound 10 after concentration, with yield of 70%, MS: 249.0 (M–H$^-$).

(3) Target Compound (Compound 11)

Use Compound 10 and 1-(4-fluorophenyl) piperazine as starting material, yellowish solid compound 11 is synthesized with yield of 20% according to synthesis method of Compound 4 in Embodiment 1.

$^1$H-NMR (400 MHz, CDCl$_3$) δ 8.62-8.64 (m, 2H), 8.14 (d, J=8.4 Hz, 1H), 8.04 (d, J=8.0. Hz, 1H), 7.93 (t, J=8.0 Hz, 1H), 7.62 (t, J=8.0 Hz, 1H), 7.52-7.55 (m, 3H), 6.98 (t, J=8.8 Hz, 1H), 6.88-6.91 (m, 2H), 4.14 (t, J=4.8 Hz, 2H), 3.52 (t, J=4.8 Hz, 2H), 3.32 (t, J=4.8 Hz, 2H), 3.08 (t, J=4.8 Hz, 2H); MS: 413.1 (M+H$^+$), 435.1 (M+Na$^+$).

Embodiment 6

(4-(5-fluoropyrimid-2-yl)piperazinyl)(2-phenylquinazolinyl) ketone (Compound 12)

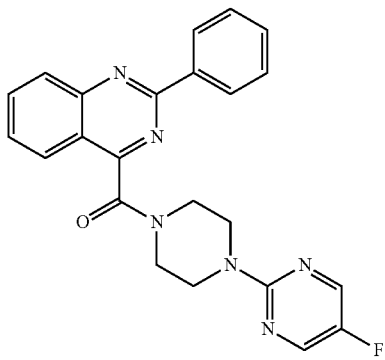

12

Use Compound 10 and 4-(5-fluoro pyrimidin-2-yl)piperazine as starting material, yellowish solid compound 12 is synthesized with yield of 82% according to synthesis method of Compound 4 in Embodiment 1.

$^1$H-NMR (400 MHz, CDCl$_3$) δ 8.61-8.64 (m, 2H), 8.22 (s, 2H), 8.14 (d, J=8.4 Hz, 1H), 8.04 (d, J=8.4 Hz, 1H), 7.94 (t, J=8.0 Hz, 1H), 7.62 (t, J=8.0 Hz, 1H), 7.52-7.55 (m, 3H), 4.04-4.14 (m, 4H), 3.82 (t, J=5.2 Hz, 2H) 3.44 (t, J=5.2 Hz, 2H); MS: 415.1 (M+H$^+$), 437.1 (M+Na$^+$).

Embodiment 7

(4-(pyrimid-2-yl) piperazinyl) (2-phenylquinazolinyl) ketone (Compound 12a)

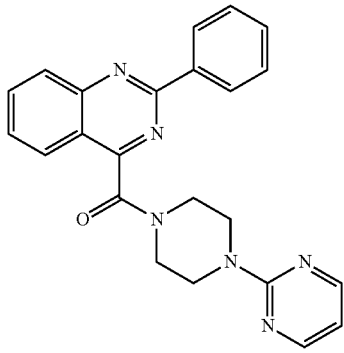

12a

Use Compound 10 and 4-(pyrimidin-2-yl) piperazine as starting material, yellowish solid compound 12 is synthesized according to synthesis method of Compound 4 in Embodiment 1.

$^1$H-NMR (400 MHz, CDCl$_3$) δ 8.61-8.64 (m, 2H), 8.32 (m, 2H), 8.14 (d J=8.4 Hz, 1H), 8.05 (d, J=8.0 Hz, 1H), 7.93 (t, J=7.2 Hz, 1H), 7.62 (t, J=7.2 Hz, 1H), 7.51-7.54 (m, 3H), 6.55 (t, J=4.4 Hz, 1H), 4.05-4.12 (m, 4H), 3.87 (t, J=5.2 Hz, 2H), 3.44 (t, J=5.2 Hz, 2H); MS: 397.1 (M+H$^+$), 419.1 (M+Na$^+$).

Embodiment 8

(4-(2-pyridinyl)piperazinyl)(2-phenylquinazolinyl) ketone (Compound 13)

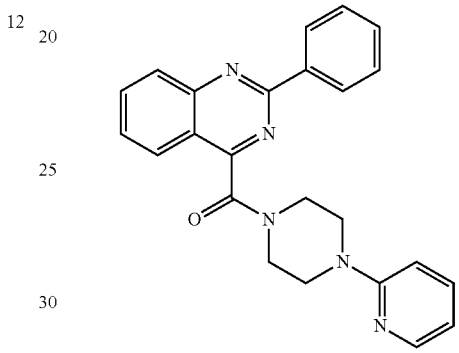

13

Use Compound 10 and 4-(pyrimidin-2-yl) piperazine as starting material, yellowish solid compound 13 is synthesized with yield of 82% according to synthesis method of Compound 4 in Embodiment 1.

$^1$H-NMR (400 MHz, CDCl$_3$) δ 8.62-8.64 (m, 2H), 8.20 (d, J=3.6 Hz, 2H), 8.14 (d, J=8.4. Hz, 1H), 8.04 (d, J=8.4 Hz, 1H), 7.93 (t, J=8.0 Hz, 1H), 7.61 (t, J=5.4 Hz, 1H), 7.48-7.53 (m, 4H), 6.65-6.69 (m, 2H), 4.08-4.14 (m, 2H), 3.78-3.80 (m, 2H), 3.51-3.59 (m, 2H), 3.46-3.49 (m, 2H); MS: 369.2 (M+H$^+$), 418.2 (M+Na$^+$).

Embodiment 9

(4-(4-fluorophenyl) piperazinyl) (pyrrol-2-yl) ketone (Compound 14)

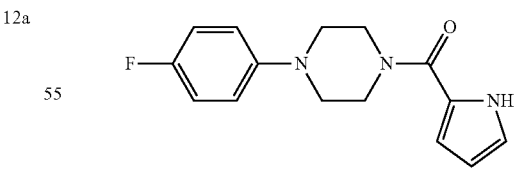

14

Use 4-(4-fluorophenyl) piperazine and pyrrole-2-carboxylic acid as starting material, white solid Compound 14 is synthesized with yield of 75% according to synthesis method of Compound 4 in Embodiment 1.

$^1$H-NMR (400 MHz, CDCl$_3$) δ 10.15 (bs, 1H) 6.96-7.02 (m, 2H), 6.86-6.95 (m, 3H), 6.56 (t, J=2.0 Hz, 1H), 6.26 (q, J=2.4 Hz, 1H), 4.01 (t, J=3.6 Hz, 4H), 3.14-3.19 (m, 4H); MS: 274.1 (M+H$^+$).

Embodiment 10

(4-(4-fluorophenyl) piperazinyl) (thien-2-yl) ketone (Compound 15)

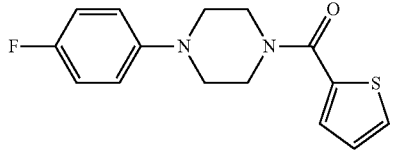

15

Use 4-(4-fluoro phenyl) piperazine and thiophene-2-carboxylic acid as starting material, white solid Compound 15 is synthesized with yield of 15% according to synthesis method of Compound 4 in Embodiment 1.

$^1$H-NMR (400 MHz, CDCl$_3$) δ 7.65 (d, J=4.8 Hz, 1H), 7.43 (d, J=5.4 Hz, 1H), 7.12 (t, J=4.0 Hz, 1H), 7 ni-7.03 (m, 4H), 3.86 (t, J=4.8 Hz, 4H), 3.18 (t, J=4.8 Hz, 4H); MS: 291.0 (M+H$^+$).

Embodiment 11

(4-(pyrimid-2-yl)piperazinyl)(indazol-3-yl)ketone (Compound 17)

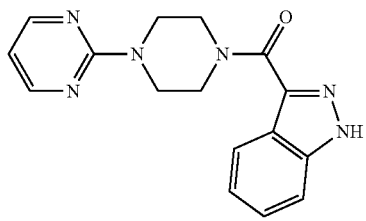

17

Use 4-(pyrimidin-2-yl) piperazine and indazole-3-carboxylic acid as starting material, white solid Compound 17 is synthesized with yield of 40% according to synthesis method of Compound 4 in Embodiment 1.

$^1$H-NMR (400 MHz, CDCl$_3$) δ 13.56 (s, 1H), 8.40 (d, J=4.8 Hz, 2H), 8.01 (d, J=8.4 Hz, 1H), 7.62 (d, J=8.0 Hz, 1H), 7.42 (t, J=7.6 Hz, 1H), 7.22 (t, J=7.6 Hz, 1H), 6.66 (t, J=4.8 Hz, 1H), 4.11 (bs, 1H), 3.83-3.84 (m, 6H); MS: 308.1 (M+H$^+$).

Embodiment 12

(4-(4-fluorophenyl)piperazinyl)(indazol-3-yl)ketone (Compound 18)

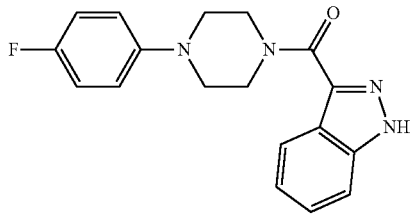

18

Use 4-(4-fluorophenyl) piperazine and indazole-3-carboxylic acid as starting material, white solid Compound 18 is synthesized with yield of 74% according to synthesis method of Compound 4 in Embodiment 1.

$^1$H-NMR (400 MHz, CDCl$_3$) δ 8.34 (d, J=8.0 Hz, 1H), 7.81-7.87 (m, 1H), 7.63-7.67 (m, 1H), 7.45-7.50 (m, 1H), 7.19-7.28 (m, 4H), 4.60 (bs, 2H), 4.25 (bs, 2H), 3.53 (bs, 4H); MS: 323.1 (M+H$^+$).

Embodiment 13

(4-(4-fluorophenyl)piperazinyl)(5-fluoroindazol-3-yl) ketone (Compound 19)

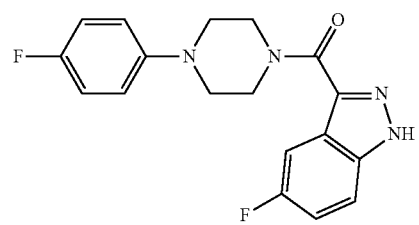

19

Use 4-(4-fluorophenyl)piperazine and 5-fluoroindazole-3-carboxylic acid as starting material, yellowish solid Compound 19 is synthesized with yield of 45% according to synthesis method of Compound 4 in Embodiment 1.

$^1$H-NMR (400 MHz, CDCl$_3$) δ 10.49 (bs, 1H), 7.84 (d, J=4.4 Hz, 1H), 7.44-7.48 (m, 1H), 7.20-7.26 (m, 1H), 6.92-7.01 (m, 4H), 4.30 (bs, 2H), 4.30 (bs, 2H), 3.20 (bs, 4H); MS: 343.1 (M+H$^+$).

Embodiment 14

(4-(4-fluorophenyl) piperazinyl) (4,7-difluoroindazol-3-yl) ketone (Compound 20)

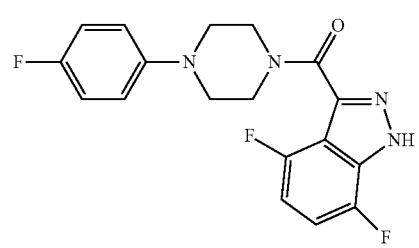

20

Use 4-(4-fluorophenyl) piperazine and 4,7-difluoroindazole-3-carboxylic acid as starting material, yellowish solid Compound 20 is synthesized with yield of 66% according to synthesis method of Compound 4 in Embodiment 1.

$^1$H-NMR (400 MHz, CH$_3$OD) δ 7.00-7.12 (m, 5H), 7.78 (bs, 1H), 4.00 (bs, 2H), 3.74 (bs, 2H), 3.23 (bs, 2H), 3.10 (bs, 2H); MS: 343.1 (M+H$^+$).

Embodiment 15

(4-(4-fluorophenyl)piperazinyl)(5-fluoroindazol-3-yl) ketone (Compound 21)

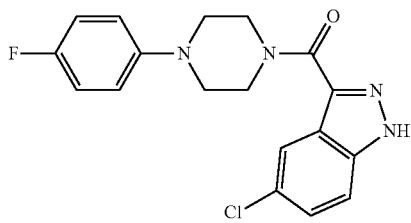

21

Use 4-(4-fluoro phenyl) piperazine and 5-fluoroindazole-3-carboxylic acid as starting material, yellowish solid Compound 21 is synthesized with yield of 51% according to synthesis method of Compound 4 in Embodiment 1.

$^1$H-NMR (400 MHz, D$_2$O) δ 7.29-7.33 (m, 3H), 7.11-7.16 (m, 4H), 3.20 (m, 8H); MS: 357.0/359.0 (3/1) (M−H'').

Embodiment 16

(4-(2-pyrimidyl)piperazinyl)(5-isopropylpyrazol-3-yl) ketone (Compound 22)

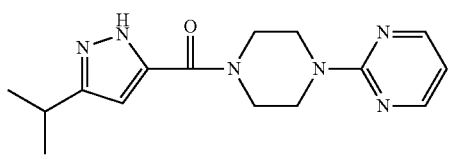

22

Use 4-(2-pyrimidinyl) piperazine and 5-isopropylpyrazole-3-carboxylic acid as starting material, white solid Compound 22 is synthesized with yield of 29% according to synthesis method of Compound 4 in Embodiment 1.

$^1$H-NMR (400 MHz, CDCl$_3$) δ 6.95-7.18 (m, 2H), 6.88-6.91 (m, 2H), 6.46 (s, 1H), 4.13 (bs, 2H), 3.15 (bs, 4H), 2.74-2.79 (m, 1H), 1.31 (d, J=6.8 Hz, 6H), MS: 317.1 (M+H$^+$).

Embodiment 17

(4-(4-fluorophenyl) piperazinyl)(5-isopropylpyrazol-3-yl) ketone (Compound 23)

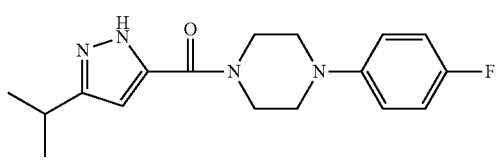

23

Use 4-(4-fluorophenyl) piperazine and 5-isopropylpyrazole-3-carboxylic acid as starting material, white solid Compound 23 is synthesized with yield of 45% according to synthesis method of Compound 4 in Embodiment 1.

$^1$H-NMR (400 MHz, CDCl$_3$) δ 11.15 (bs, 1H), 8.32 (t, J=4.0 Hz, 2H), 6.52 (d, J=4.0 Hz, 1H), 6.45 (s, 1H), 4.07 (bs, 2H), 3.90 (bs, 6H), 3.00 (t, J=7.2 Hz, 1H), 1.31 (d, J=6.8 Hz, 6H), 1.29 (d, J=6.4 Hz, 6H); MS: 317.1 (M+H$^+$).

Embodiment 18

(2-(4-fluoropyrimidyl) piperazinyl) (4-methyl-6-phenylpyridazinyl) ketone (Compound 24)

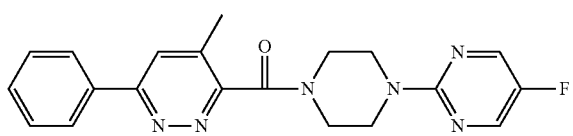

24

Use 1-(4-fluoropyrimidyl) piperazine and 3-carboxyl-4-methyl-6-phenylpyridazine as starting material, white solid Compound 24 is synthesized with yield of 72% according to synthesis method of Compound 4 in Embodiment 1.

$^1$H-NMR (CDCl$_3$): δ 8.22 (s, 2H), 8.08 (m, 2H), 7.76 (s, 1H), 7.52 (m, 3H), 3.96 (s, 4H), 3.84 (dd, J=5.2 Hz, J=3.2 Hz, 2H), 3.48 (dd, J=3.2 Hz, J=3.2 Hz, 2H), 2.47 (s, 3H). MS (ESI): [M+H]$^+$ 379.1, [M+Na]$^+$ 401.1.

Embodiment 19

(2-pyrazinylpiperazinyl) (4-methyl-6-phenylpyridazinyl) ketone (Compound 25)

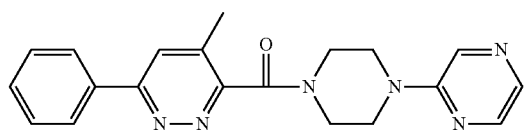

25

Use 1-(2-pyrazinyl) piperazine and 3-carboxyl-4-methyl-6-phenylpyridazine as starting material, white solid Compound 25 is synthesized with yield of 82% according to synthesis method of Compound 4 in Embodiment 1.

$^1$H NMR (CDCl$_3$): δ 8.19 (d, J=3.2 Hz, 1H), 8.10 (m, 3H), 7.92 (d, J=3.2 Hz, 1H), 7.77 (s, 1H), 7.53 (m, 3H), 4.03 (dd, J=4.S Hz, J=3.2 Hz, 2H), 3.81 (dd, J=3.2 Hz, J=4.8 Hz, 2H), 3.70 (dd, J=4.8 Hz, J=3.2 Hz, 2H), 3.60 (dd, J=3.2 Hz, J=4.S Hz, 2H), 2.49 (s, 3H). MS (ESI): [M+H]+ 361.1.

Embodiment 20

(N-methylpiperazinyl) (4-methyl-6-phenylpyridazinyl) ketone (Compound 26)

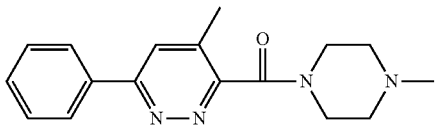

26

Use 1-methyl piperazine and 3-carboxyl-4-methyl-6-phenylpyridazine as starting material, yellowish solid Compound 26 is synthesized with yield of 75% according to synthesis method of Compound 4 in Embodiment 1.

$^1$H NMR (CDCl$_3$): δ 8.06 (m, 2H), 7.72 (s, 1H), 7.50 (m, 3H), 3.89 (bs, 2H), 3.40 (t, J=4.8 Hz, 2H), 2.54 (t, J=4.8 Hz, 2H), 2.43 (m, 5H), 2.31 (s, 3H). MS (ESI): [M+H]$^+$ 297.1, [M+Na]$^+$ 319.1.

Embodiment 21

(N-isopropylpiperazinyl) (4-methyl-6-phenylpyridazinyl) ketone (Compound 27)

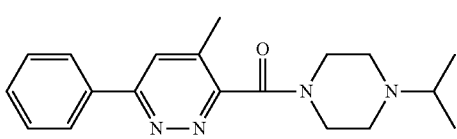

27

Use N-isopropylpiperazine and 3-carboxyl-4-methyl-6-phenylpyridazine as starting material, yellowish solid Compound 27 is synthesized with yield of 60% according to synthesis method of Compound 4 in Embodiment 1.

$^1$H NMR (CDCl$_3$): δ 8.08 (m, 2H), 7.74 (s, 1H), 7.53 (m, 3H), 3.90 (t, J=4.8 Hz, 2H), 3.41 (t, J=4.8 Hz, 2H), 2.76 (m, 1H), 2.66 (t, J=4.8 Hz, 2H), 2.55 (t, J=4.8 Hz, 2H), 2.46 (s, 3H), 1.06 (d, J=6.4 Hz, 6H). MS (ESI): [M+H]$^+$ 325.1.

Embodiment 22

(N-cyclohexylpiperazinyl) (4-methyl-6-phenylpyridazinyl) ketone (Compound 28)

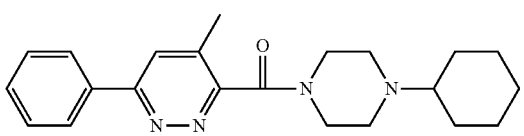

28

Use N-cyclohexylpiperazine and 3-carboxyl-4-methyl-6-phenylpyridazine as starting material, yellowish solid Compound 28 is synthesized with yield of 80% according to synthesis method of Compound 4 in Embodiment 1.

$^1$H NMR (CDCl$_3$): δ 8.09 (m, 2H), 7.74 (s, 1H), 7.53 (m, 3H), 3.90 (t, J=4.8 Hz, 2H), 3.40 (t, J=4.8 Hz, 2H), 2.72 (t, J=4.8 Hz, 2H), 2.60 (t, J=4.8 Hz, 2H), 2.45 (s, 3H), 2.33 (m, 1H), 1.84 (m, 4H), 1.62 (m, 2H), 1.24 (m, 4H). MS (ESI): [M+H]$^+$ 365.2.

Embodiment 23

(4-(4-pyridinyl) piperazinyl)(2-phenylquinazolinyl) ketone (Compound 34)

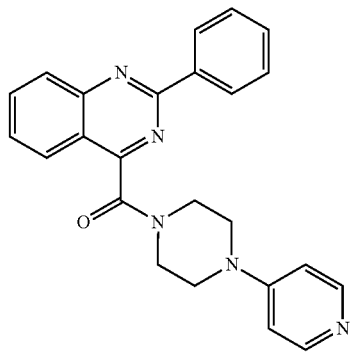

34

Use Compound 10 and 4-pyridinyl piperazine as starting material, yellowish solid Compound 34 is synthesized with yield of 75% according to synthesis method of Compound 4 in Embodiment 1.

$^1$H NMR (CDCl$_3$): δ 8.63 (m, 2H), 8.30 (bs, 2H), 8.15 (d, J=8.4 Hz, 1H), 8.04 (d, J=8.4. Hz, 1H), 7.95 (t, J=7.2 Hz, 1H), 7.65 (t, J=7.2 Hz, 1H), 6.71 (d, /=4.8 Hz, 1H), 4.13 (t, /=4.8 Hz, 2H), 3.65 (t, /=4.8 Hz, 2H), 3.56 (t, /=4.8 Hz, 2H), 3.42 (t, /=4.8 Hz, 2H). MS (ESI): [M+H]$^+$ 396.0.

Embodiment 24

(4-(2-pyrazinyl) piperazinyl) (2-phenylquinazolinyl) ketone (Compound 35)

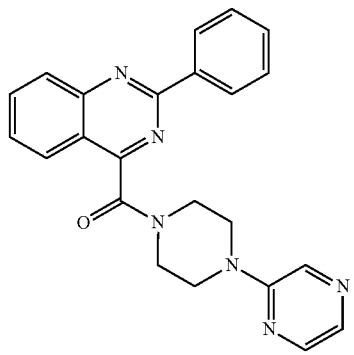

35

Use Compound 10 and 4-(2-pyrazinyl) piperazine as starting material, white solid Compound 35 is synthesized with yield of 81% according to synthesis method of Compound 4 in Embodiment 1.

$^1$H NMR (CDCl$_3$): δ 8.62 (m, 2H), 8.16 (m, 2H), 8.10 (s, 1H), 8.04 (d, J=8.4 Hz, 1H), 7.93 (m, 2H), 7.64 (t, J=1.6 Hz, 1H), 7.55 (m, 3H), 4.13 (m, 2H), 3.85 (m, 2H), 3.65 (m, 2H), 3.52 (m, 2H). MS (ESI): [M+H]$^+$ 397.2.

Embodiment 25

(4-methylpiperazinyl) (2-phenylquinazolinyl) ketone (Compound 36)

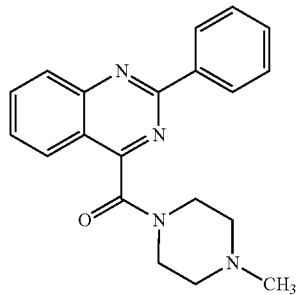

Use Compound 10 and 4-methylpiperazine as starting material, yellowish solid Compound 36 is synthesized with yield of 35% according to synthesis method of Compound 4 in Embodiment 1.

$^1$H NMR (CDCl$_3$): δ 8.62 (m, 2H), 8.14 (d, J=8.4 Hz, 1H), 8.03 (d, J=8.4 Hz, 1H), 7.94 (dt, J=0.8, J=7.2 Hz, 1H), 7.62 (dt, J=0.8, J=7.2 Hz, 1H), 7.51 (m, 3H), 4.01 (t, J=5.2 Hz, 2H), 3.37 (t, J=5.2 Hz, 2H), 2.63 (t, J=5.2 Hz, 2H), 2.38 (t, J=5.2 Hz, 2H). MS (ESI): [M+H]$^+$333.2.

Embodiment 26

(4-isopropylpiperazinyl)(2-phenylquinazolinyl)ketone (Compound 37)

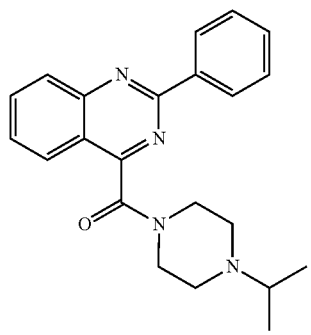

Use Compound 10 and 4-isopropylpiperazine as starting material, yellowish solid Compound 37 is synthesized with yield of 35% according to synthesis method of Compound 4 in Embodiment 1.

$^1$H NMR (CDCl$_3$): δ 8.63 (m, 2H), 8.14 (d, J=8.4 Hz, 1H), 8.01 (d, J=8.4 Hz, 1H), 7.94 (dt, J=0.8, J=7.2 Hz, 1H), 7.62 (dt, J=0.8, J=7.2 Hz, 1H), 7.52 (m, 3H), 3.99 (t, J=4.8 Hz, 2H), 3.34 (t, J=4.8 Hz, 2H), 2.73 (t, J=4.8 Hz, 2H), 2.47 (t, J=4.8 Hz, 2H). MS (ESI): [M+H]$^+$361.2.

Embodiment 27

(cyclohexylpiperazinyl) (2-phenylquinazolinyl) ketone (Compound 38)

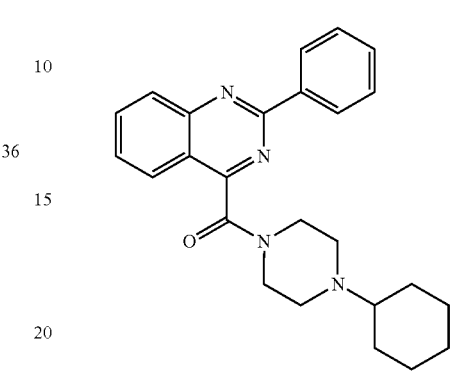

Use Compound 10 and 4-cyclohexylpiperazine as starting material, yellowish solid Compound 38 is synthesized with yield of 88% according to synthesis method of Compound 4 in Embodiment 1.

$^1$H NMR (CDCl$_3$): δ 8.63 (m, 2H), 8.11 (d, J=8.4 Hz, 1H), 8.01 (d, J=8.4 Hz, 1H), 7.93 (dt, J=1.2, J=7.2 Hz, 1H), 7.61 (dt, J=0.8, J=7.2 Hz, 1H), 7.52 (m, 3H), 3.97 (t, J=4.8 Hz, 2H), 3.33 (t, J=4.8 Hz, 2H), 2.77 (t, J=4.8 Hz, 2H), 2.50 (t, J=4.8 Hz, 2H), 2.30 (m, 1H), 1.83 (m, 4H), 1.63 (m, 2H), 1.23 (m, 4H). MS (ESI): [M+H]$^+$ 401.3.

Embodiment 28

Activity Determination In Vitro

The activity test of the compound of the present application use the known method in the field, and the compound for testing is prepared using the above mentioned method in embodiments. Evaluate the potential application value according to the efficiency of specific inhibition of candidate compound to IL-Iβ secretion of microglial cell.

The research show that microglial cell is the cell type that response first when central nervous system is injured, and a variety of pathological states of the central nervous system can activate microglial cell, for example, trauma, cerebral stroke, inflammatory response and neurodegenerative disease etc. Activated microglial cells are involved in many types of pathological states, for example, activated microglial cells can result in motor neuron injury by releasing free radicals. The patients of Parkinson's disease and animal models of Parkinson's disease have a large number of increasement of microglial cells, except a large number of dopaminergic neurons of black mass density are in the necrosis, and these activated microglial cells can produce a large number of superoxide radicals, which are considered as the major reason for leading the dopaminergic neurons necrosis in the brains of the patients of Parkinson's disease. Around the areas of senile plaques in the brain of the patients of Parkinson's disease, there are a lot of activated microglial cells, and these microglial cells, by releasing cytokines, induce the production of amyloid precursor protein (APP) of neuron and astrocyte; the aggregation of APP is the major reason for AD. Many evidences show that apoptosis of nerve cells is closely related to activation of microglial cells; β amyloid protein activates immuno-inflammatory responses mediated by microglial cells, which leads to specific cell apoptosis and cognitive disorder. Inflammatory factors like TNF-α, released by activated microglial cells can injury oligodendroglia cells and myelin sheath, and lead to multiple sclerosis (MS).

In addition, the activation of microglial cells plays an important role in production and maintenance of neuropathic pain. Under the pain stimulation, microglial cells are activated, and Kaiyuan FU found that (FU, Kaiyuan, Spinal Microglial Reactions induced by peripheral inflammatory pain stimulation, Chinese Journal of Neuroimmunology and Neurology 2001, 8: 179-183). After stimulation of formalin, algogenic substance of peripheral inflammatory pain, increasement of microglial cells is activated, that may be one of the reasons of long lasting chronic pain. Drug for example, fluorocitrate, which inhibits function of microglial cells, show have significant abirritation, indicating that activation of microglial cells has close relevance with production and maintenance of neuropathic pain.

In recently years, the research show that children with epilepsy also have low immunologic function; microglial cell is the macrophage of central nervous system, and plays an important role in start, development, prognosis procedures of immune inflammatory response in the brain. Astrocytes degeneration and necrosis induced by activation of microglial cells may be an important physiological path of epilepsy.

Currently during some treatment of nerve inflammatory disease, research on drug inhibiting the activation of microglial cells gets more and more attention. In central nerve system, level of IL-1β plays an important role in the conversion of microglial cell from selection status to activation status. So the applicant evaluates the potential application value according to the efficiency of specific inhibition of candidate compound to IL-1β secretion of microglial cell.

Experimental Method:

1. Rat microglial cell $BV_2$ and Glioma cell line C6 are incubated in DMEM culture medium with 10% FBS, and the $6^{th}$ to $15^{th}$ generation culture cells are applicable for compound activity selection. Culture cells are innoculated on the 24-well cell culturing plate with 50,000 cells/well, after one day culturing, switch to low serum medium (with 2% FBS) for another 16 hours culturing. Add 300 ng/ml (for induction of $BV_2$ cells) or 1 mg/mL (for induction of $C_6$ cells) LPS (*Salmonella typhimutium*) to the culture medium to induce the IL-1β secretion of culture cells. At the same time, add sample to be determined (with DMSO≤0.1%) at concentrations of 200 pM, 20 nM, 2 μM and 200 μM; add 0.1% DMSO to blank as solvent control.

2. 24 hours after LPS induction/drug treatment, collect the culture solution and quantitatively measure the level of IL-1β. Centrifuge the culture solution at 8,000 g for 10 min at 4° C., and remove the floating particle impurities. Dilute the supernant one time, and take 150 μL sample for ELISA (Biosource) measurement.

3. Treatment of culture cells and ELISA measurement are conducted with double blind method.

4 Inhibition efficiency of candidate compound is calculated according to formula, and $IC_{50}$ of every kind of candidate compound is calculated.

Inhibition efficiency(%)=([IL-1β]$_{LPS\ induction}$−[IL-1β]$_{medical\ treatment}$)/[IL-1β]$_{LPS\ induction}$×100%.  Formula 5. Efficiency evaluation of candidate compound: positive inhibition rate of compound to IL-1β secretion of $BV_2$ is the standard judgment of compounds efficiency; negative inhibition rate of compound to IL-1β secretion of $C_6$ is the standard judgment of compounds safety.

Experimental Result:

TABLE 1

$IC_{50}$ of inhibition of the compounds of the present application to IL-1β secretion of $BV_2$

| Group | $IC_{50}$ |
|---|---|
| Compound 20 | 42.53 nM |
| Compound 4 | 0.56 nM |
| Compound 5 | 0.6 nM |
| Compound 11 | 3.38 nM |
| Compound 12 | 1.42 nM |
| Compound 13 | 24.32 nM |
| Compound 12a | 0.16 nM |
| Compound 24 | 5.49 nM |
| Compound 26 | 0.11 nM |

TABLE 2

Inhibition rate of the compounds of the present application to the IL-1β secretion of $BV_2$ at concentration of 20 nM

| Group | Inhibition rate (%) at 20 nM |
|---|---|
| Compound 20 | 48.0639 ± 0.0618 |
| Compound 4 | 54.6064 + 0.0117 |
| Compound 5 | 54.5398 + 0.0357 |
| Compound 12a | 46.1355 + 0.0571 |

The experimental results show that the compound of the present invention can inhibit the IL-1β secretion of $BV_2$ with high efficiency, and $IC_{50}$ can be as low as nM. When the concentration is 20 nM, inhibition rate of the compounds of the present application to the IL-1β secretion of $BV_2$ all exceeded or got close to 50%.

All content of patents, patent application publication, patent applications, and non-patent publication as mentioned in the specification are introduced as reference.

What is claimed is:

1. A compound represented by formula (I) and the pharmaceutical acceptable salt thereof,

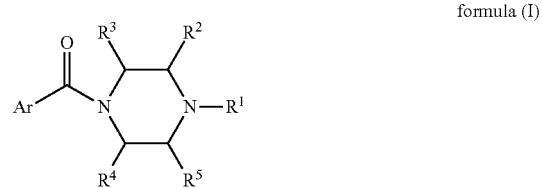

formula (I)

wherein, $R^1$ is selected from the group consisting of hydrogen, substituted or unsubstituted alkyl, substituted or unsubstituted cyclic alkyl, substituted or unsubstituted aryl, substituted or unsubstituted heterocyclic aryl, and substituted or unsubstituted heterocyclic alkyl, wherein the substituents are selected from the group consisting of aryl, aryl alkyl, alkyl, alkoxy, halogenated alkyl, halogen, hydroxyl, azyl, and cyano group;

$R^2$, $R^3$, $R^4$, $R^5$ are independently selected from the group consisting of hydrogen, hydroxyl, azyl, cyano group, halogen, alkyl, alkoxy, cycloalkyl, aryl, aryl alkyl, heterocyclic aryl and heterocyclic alkyl; and Ar is 4 methyl-6-phenylpyridazin-3-yl.

2. The compound represented by formula (I) and the pharmaceutical acceptable salt thereof according to claim 1, wherein $R^1$ is a substituted or unsubstituted $C_1$-$C_6$ alkyl, substituted or unsubstituted $C_3$-$C_{10}$ cyclic alkyl, substituted or unsubstituted $C_6$-$C_{10}$ aryl, or substituted or unsubstituted 5-10 members heterocyclic aryl, wherein the substituents are selected from the group consisting of aryl, aryl alkyl, alkyl, alkoxy, halogenated alkyl, halogen, hydroxyl, azyl, and cyano group.

3. The compound represented by formula (I) and the pharmaceutical acceptable salt thereof according to claim 1, wherein $R^1$ is a 4-fluoro phenyl, 2,4-bifluoro phenyl, pyrimidin-2-yl, pyridin-2-yl, 5-fluoropyrimidin-2-yl, pyrazin-2-yl, pyridin-4-yl, methyl, isopropyl or cyclohexyl.

4. The compound represented by formula (I) and the pharmaceutical acceptable salt thereof according to claim 1, wherein $R^2$, $R^3$, $R^4$, $R^5$ are individually hydrogen.

5. The compound represented by formula (I) and the pharmaceutical acceptable salt thereof according to claim 1, selected from the following compounds and the pharmaceutical acceptable salts thereof:
- (4-(4-fluorophenyl)-1-piperazinyl)(4-methyl-6-phenyl-3-pyridazinyl) ketone;
- (4-(2,4-difluorophenyl)-1-piperazinyl)(4-methyl-6-phenyl-3-pyridazinyl) ketone;
- (4-(2-pyrimidyl)-1-piperazinyl) (4-methyl-6-phenyl-3-pyridazinyl) ketone;
- (4-(2-pyridinyl)-1-piperazinyl) (4-methyl-6-phenyl-3-pyridazinyl) ketone;
- (4-(5-fluoro-2-pyrimidyl)-1-piperazinyl)(4-methyl-6-phenyl-3-pyridazinyl) ketone;
- (4-(2-pyrazinyl)-1-piperazinyl) (4-methyl-6-phenyl-3-pyridazinyl) ketone;
- (N-methyl-1-piperazinyl) (4-methyl-6-phenyl-3-pyridazinyl) ketone;
- (N-isopropyl-1-piperazinyl) (4-methyl-6-phenyl-3-pyridazinyl) ketone; or
- (N-cyclohexyl-1-piperazinyl) (4-methyl-6-phenyl-3-pyridazinyl) ketone.

6. A method for preparing a compound and the pharmaceutical acceptable salt thereof according to claim 1, comprising a reaction as following:

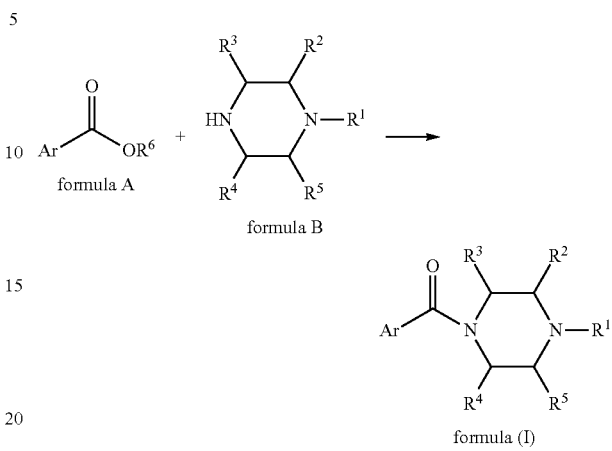

wherein $R^1$, $R^2$, $R^3$, $R^4$, $R^5$, Ar are defined same as claim 1, $R^6$ is a hydrogen or alkyl; and if needed, a compound with formula (I) is converted into the pharmaceutical acceptable salt thereof.

7. The method according to claim 6, wherein the method is conducted in the presence of a condensating agent, which is N,N-dicyclohexylcarbodiimide (DCC), N,N-diisopropylcarbodiimide (DIC), N-ethylcarbonimidoyl-N,N-dimethylpropane-1,3-diamine (EDC) or 1-ethyl-(3-dimethylaminopropyl)carbodiimide hydrochloride (EDCI).

8. A pharmaceutical composition, comprising a pharmaceutical acceptable carrier and a compound represented by formula (I) or the pharmaceutical acceptable salt thereof according to claim 1.

* * * * *